US012594053B2

(12) United States Patent
Shoudy et al.

(10) Patent No.: US 12,594,053 B2
(45) Date of Patent: Apr. 7, 2026

(54) PATIENT-SPECIFIC NEUROMODULATION ALIGNMENT STRUCTURES

(71) Applicant: GE Precision Healthcare LLC, Wauwatosa, WI (US)

(72) Inventors: David Andrew Shoudy, Niskayuna, NY (US); Craig Patrick Galligan, Averill Park, NY (US); Weston Blaine Griffin, Niskayuna, NY (US); Jeffrey Michael Ashe, Gloverville, NY (US); Warren Lee, Niskayuna, NY (US); James Enrico Sabatini, Scotia, NY (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 66 days.

(21) Appl. No.: 18/520,180

(22) Filed: Nov. 27, 2023

(65) Prior Publication Data

US 2024/0090869 A1     Mar. 21, 2024

Related U.S. Application Data

(63) Continuation of application No. 17/319,741, filed on May 13, 2021, now Pat. No. 11,826,197.

(51) Int. Cl.
*A61B 8/00* (2006.01)
*A61N 7/00* (2006.01)

(52) U.S. Cl.
CPC .......... *A61B 8/4227* (2013.01); *A61B 8/4254* (2013.01); *A61N 7/00* (2013.01);
(Continued)

(58) Field of Classification Search
CPC ..... A61B 8/4227; A61B 8/4254; A61B 8/429; A61B 8/4411; A61B 8/4416; A61B 8/46;
(Continued)

(56) References Cited

U.S. PATENT DOCUMENTS

| | | | |
|---|---|---|---|
| 6,122,542 | A | 9/2000 | Lee et al. |
| 7,410,469 | B1 | 8/2008 | Talish et al. |

(Continued)

FOREIGN PATENT DOCUMENTS

| | | |
|---|---|---|
| CN | 10039600 B | 10/2018 |
| JP | 2013541383 A | 11/2013 |
| WO | 2015023787 A1 | 2/2015 |

OTHER PUBLICATIONS

Ativanichayapohong, Thermpon, et al.; A Combined Wireless Neural Stimulating and Recording System for Study of Pain Processing; Journal of Neuroscience Methods, vol. 170, Issue 1, May 15, 2008; pp. 25-34.

(Continued)

*Primary Examiner* — Alexei Bykhovski
(74) *Attorney, Agent, or Firm* — Fletcher Yoder, P.C.

(57) ABSTRACT

The present discussion relates to structures and devices to facilitate application of an ultrasound therapy beam to a target anatomic region in a replicable manner. In certain aspects, adjustable positioning structures are described that allow a general probe positioning structure to be configured for a specific patient in a manner that allows the device to be used repeatedly to target the anatomic region, even when in non-clinical settings. In other aspects, a probe positioning structure is fabricated that is specific to a respective patient anatomy, such that use of the probe positioning structure provides repeatable targeting of the target anatomic region, even when in non-clinical settings.

18 Claims, 18 Drawing Sheets

(52) U.S. Cl.
CPC ................. *A61N 2007/0026* (2013.01); *A61N*
*2007/0052* (2013.01); *A61N 2007/0078*
(2013.01)

(58) Field of Classification Search
CPC ........ A61B 2090/064; A61B 2090/378; A61B
8/4427; A61B 8/4477; A61B 8/08; A61N
7/00; A61N 2007/0026; A61N 2007/0052;
A61N 2007/0078; A61N 7/02
See application file for complete search history.

(56) References Cited

U.S. PATENT DOCUMENTS

| | | |
|---|---|---|
| 8,374,701 B2 | 2/2013 | Hyde et al. |
| 8,725,251 B2 | 5/2014 | Della Rocca et al. |
| 9,199,096 B2 | 12/2015 | Lewis, Jr. |
| 9,440,070 B2 | 9/2016 | Goodwasser et al. |
| 9,545,221 B2 | 1/2017 | Adhikari et al. |
| 10,002,424 B2 | 6/2018 | Yu et al. |
| 10,327,624 B2 | 6/2019 | Huang et al. |
| 10,413,757 B2 | 9/2019 | Sato et al. |
| 10,531,858 B2 | 1/2020 | Lachaine et al. |
| 10,532,211 B2 | 1/2020 | Ghaffari et al. |
| 2009/0149782 A1 | 6/2009 | Cohen |
| 2011/0077514 A1 | 3/2011 | Ulric et al. |
| 2011/0172672 A1 | 7/2011 | Dubeau et al. |
| 2011/0251489 A1* | 10/2011 | Zhang ................. A61B 8/4227 |
| | | 600/459 |
| 2012/0157889 A1 | 6/2012 | Tanis |
| 2012/0253239 A1 | 10/2012 | Gertner |
| 2013/0289411 A1 | 10/2013 | Barnard et al. |
| 2015/0080942 A1* | 3/2015 | Garrison ................. A61B 8/06 |
| | | 606/202 |
| 2016/0008632 A1 | 1/2016 | Wetmore et al. |
| 2016/0331952 A1 | 11/2016 | Faltys et al. |
| 2017/0065835 A1* | 3/2017 | Park ...................... A61B 6/501 |
| 2017/0209717 A1 | 7/2017 | Bonutti et al. |
| 2017/0263020 A1 | 9/2017 | Huang et al. |
| 2018/0207450 A1 | 7/2018 | Sanchez et al. |
| 2018/0229057 A1 | 8/2018 | Fontanarosa |
| 2020/0054414 A1 | 2/2020 | Wagner |
| 2020/0069976 A1* | 3/2020 | Puleo ..................... A61B 90/96 |
| 2020/0075171 A1 | 3/2020 | Lampo |
| 2020/0306564 A1 | 10/2020 | Bar-Zion et al. |

OTHER PUBLICATIONS

"Sam@ Sport" retrieved from https://samrecover.com/sam-sport/.
JP application 2023-569783 filed Nov. 10, 2023—Office Action issued Aug. 21, 2024; Machine Translation; 11 pages.
EP application 22808087.5 filed Nov. 14, 2023—extended Search Report issued Feb. 11, 2025; 11 pages.

* cited by examiner

454A

580

454B

582

PATIENT-SPECIFIC NEUROMODULATION ALIGNMENT STRUCTURES

CROSS-REFERENCE TO RELATED APPLICATIONS

The present application is a continuation of U.S. application Ser. No. 17/319,741, entitled PATIENT-SPECIFIC NEUROMODULATION ALIGNMENT STRUCTURES, and filed on May 13, 2021 the disclosure of which is incorporated by reference herein in its entirety.

BACKGROUND

The subject matter disclosed herein relates to targeting and/or dosing regions of interest in a subject via application of neuromodulating energy to cause targeted physiological outcomes. In particular, the disclosed techniques may be useful in helping an untrained person provide repeated treatments to a targeted region.

Neuromodulation has been used to treat a variety of clinical conditions. However, specific tissue targeting via neuromodulation may be challenging. For example, accurate focusing of neuromodulating energy may vary based on individual patient anatomy. Certain patients may have variations in organ size or location relative to other patients based on their height, weight, age, gender, clinical condition, and so forth, which may impact targeting and dose delivery when using various neuromodulation techniques.

In the context of neuromodulation using ultrasonic devices, other common challenges may relate to the difficulty in repeatedly delivering accurate and consistent ultrasonic therapy at a prescribed dose in the context of a treatment regime involving multiple, repeated treatments of the treatment region. Further such treatments may be difficult for a minimally trained person to administer, making it necessary for the patient to enter a clinical setting and/or be treated by medically trained personnel for each treatment session. Treatment by the patient themselves, or in a home setting, is therefore not typically considered feasible for an ultrasound-based neuromodulation regime.

For example, when a clinician administers a conventional ultrasound exam, the clinician places the probe on the body and maneuvers in all degrees-of-freedom (DOFs) until they arrive at the target scan plane. In contrast, in a patient or self-administered, at-home context, the untrained user has near zero capacity to understand an ultrasound image, even if available, and intelligently maneuver a handheld ultrasound probe to find the target. Such issues make self-administration of precisely targeted ultrasonic based treatments, particularly in an at-home context, impractical using conventional approaches.

BRIEF DESCRIPTION

The disclosed embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a wearable device is provided. In accordance with this embodiment, the wearable device comprises an ultrasound probe and a positioning structure configured to hold the ultrasound probe. The ultrasound probe comprises one or more ultrasound transducers. One or more of the ultrasound transducers are configured to emit a therapy beam and one or more of the ultrasound transducers are configured to emit an imaging beam.

In another embodiment, a method of configuring a wearable device is provided. In accordance with this embodiment, the wearable device is applied to a subject. An ultrasound probe is coupled to a positioning structure of the wearable device. The ultrasound probe comprises one or more ultrasound transducers. One or more of the ultrasound transducers are configured to emit a therapy beam and one or more of the ultrasound transducers are configured to emit an imaging beam. One or more of the wearable device, the positioning structure, or the ultrasound probe are adjusted with respect to an anatomic target region of the subject. One or more fitting parameters of the wearable device, the positioning structure, or the ultrasound probe, when aligned to the anatomic target region, are determined. The one or more parameters are saved for use when the wearable device is subsequently applied to the subject for a therapy session.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
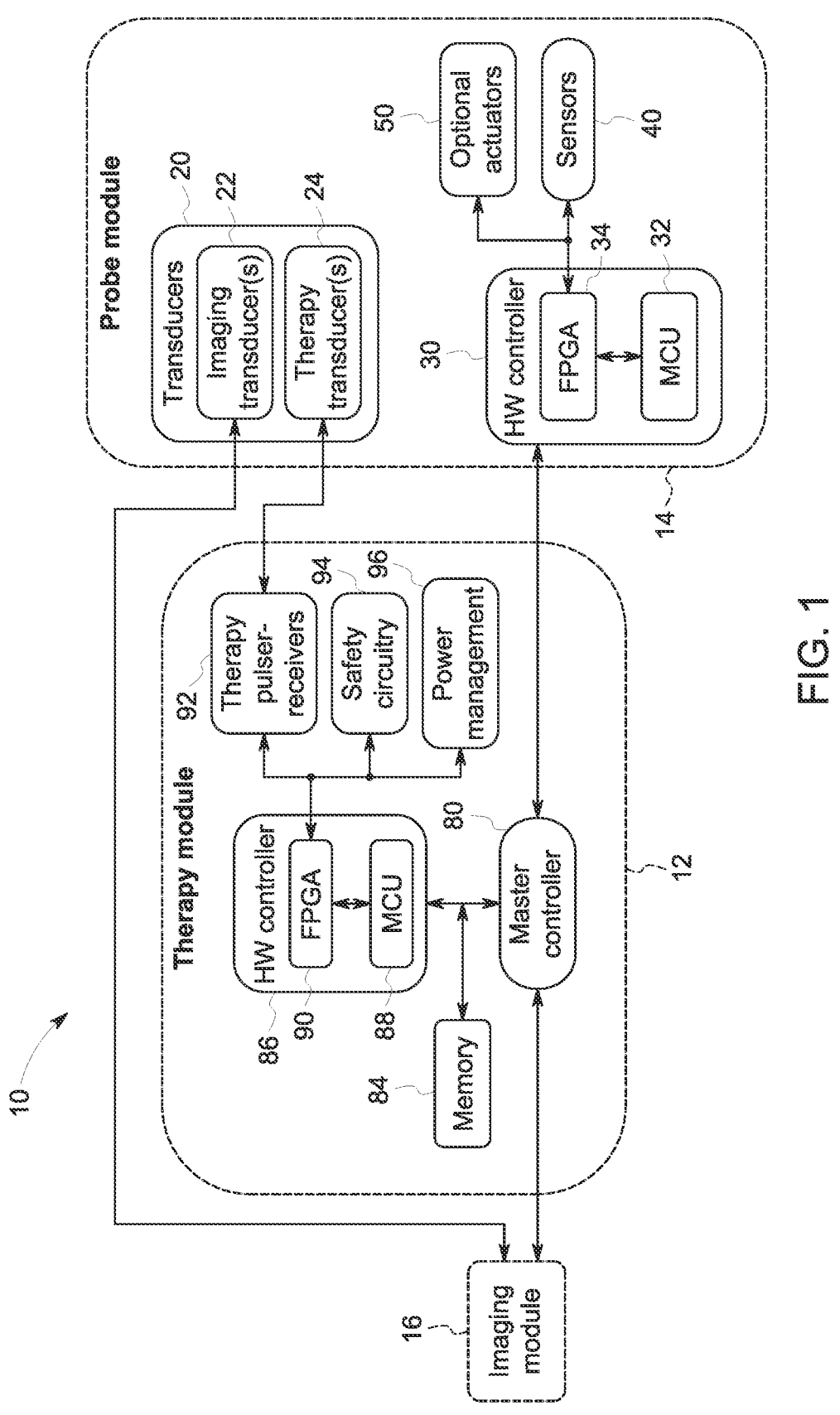
FIG. 1 is a block diagram of a neuromodulation delivery system according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments," "in some embodiments," and "in one (an) embodiment."

As discussed herein, one issue that can arise with respect to therapy techniques that involve multiple sessions (e.g., 1× per day, 3× per week, 1× per week) of targeted ultrasonic neuromodulation is the need to provide consistent, correct alignment for each session. In the context of a therapy capable of being implemented in non-clinical settings (e.g., at home) by individuals with little or no medical training (including patients) it is desirable that such targeting and alignment guidance be provided in as simple a format as possible. For example, it may be desirable to provide targeting and/or alignment assistance without manual guidance based on displayed images and/or with common sources of user error or frustration removed or minimized. In addition, it may further be useful to use one type of alignment device that is suitable for use across a wide patient population, despite the fact that a "one size fits all approach" is not feasible due to the large variation in patient internal and external anatomy. With this in mind the presently described approaches, structures, and techniques encompass ultrasound therapy alignment devices having customizable elements and/or that are otherwise personalized for each patient's unique external body shape and size and to the patient's internal anatomy shape, size, and location. The systems and devices are customizable to address the large variability in the overall patient population, while also being suitable for use in non-clinical settings (e.g., home use by the patient).

By way of example, in certain embodiments discussed herein an alignment device is provided as a wearable ultrasound therapy alignment device (e.g., a belt, a vest, and so forth) that includes configurable sizing or adjustment features, settings, optional swappable components, and/or sensors for personalization. Protocols are also provided for determining the personalized settings and for the fit of the alignment device to configure a given alignment device to a patient for a respective therapy target (i.e., fitting protocols) and protocols are also described for the use of a fitted alignment device in a therapy session administered in a non-clinical setting, such as at the home (i.e., use protocols). After customization, the personalized sizing and/or alignment features enable repeatable positioning on the body of the respective patient and nominally aim and focus the ultrasound therapy beam at the internal anatomy target. Such a target region may be a portion or sub-portion of a larger organ or structure, such as the porta-hepatis region within the liver or hilum region within the spleen.

To address the uniqueness of each patient's overall body shape and size, as well as the selected external location on the body, the wearable alignment device has customizable sizing, adjustable ultrasonic probe placement, and features to secure the probe in place in a repeatable manner and for hands-free operation. To address the uniqueness of each patient's internal anatomy, the alignment device may include angular adjustments (e.g., rock, tilt, spin) and configurable depth to nominally point and focus the therapy beam at the target region. Further, in some embodiments, after the location of the target is determined, the system may be configured to deliver therapy at that location by electronically steering the therapy beam to the determined location when applying a therapy dose. Alternatively, a therapy transducer having appropriate therapy transducer characteristics (e.g., power handling, frequency range, geometry and so forth) and/or a probe cap having a suitable probe cap characteristics (e.g., angular adjustment, attenuation adjustment (for example, standoff height and/or composition), other geometries or features useful for focusing, shaping, or targeting the beam, and so forth) may be selected and employed to direct the therapy beam to the determined location when applying a therapy dose.

When determining the personalized settings as part of a fitting session, physical features that enable locking and unlocking the adjustments, and digital features that enable storage of baseline target depth, target location within the imaging plane, baseline image data for comparison, and other sensor readings may be employed. When in use in a non-clinical setting (e.g., the home), the patient or other user may be guided to position the alignment device on the selected external location on the body, secure (e.g., lock) the alignment device in place, and perform fine adjustments to achieve the desired alignment. The alignment device may leverage prior information stored for the patient as well as online sensor data and a live ultrasound image, if available, to ensure proper fit and probe placement.

In further examples, certain implementations discussed herein utilize an alignment device or structure that is custom fabricated or molded to fit a patient's external anatomy to ensure repeatable, accurate alignment to an internal ultrasound stimulation target region. Use of a custom fabrication system may allow an untrained user in a non-clinical setting (e.g., a patient in their home) to safely conduct ultrasonic stimulation of a specific neural target region over multiple sessions without the need for assistance from a sonographer or clinician. In particular, in such implementations a custom fabrication process may be employed that reproduces the initial placement accuracy of the therapy transducer. This, in turn, may allow therapy to be performed solely by the patient, such as in his or her own home. That is, such a custom fabricated structure can be used to repeatedly position the transducer in generally correct alignment with respect to a given patient, thereby allowing the patient to self-administer ultrasonic neuromodulation to an internal target region. The degree of target alignment thereby provided is improved relative to unguided positioning without the assistance of a custom fabricated fixture. In particular, the target alignment relative to the neural target region is improved due to the customized nature of the alignment device, which may utilize patient-specific anatomical features to anchor the therapy transducer in the correct position and orientation.

With this in mind, FIG. 1 depicts an example of a neuromodulation system configured to be used to deliver neuromodulating energy as part of a treatment protocol and which may be used with an alignment and/or positioning device or structure as discussed herein. In particular, FIG. 1 is a schematic representation of a system 10 for neuromodulation to achieve neuromodulating effects such as neurotransmitter release and/or activation of components (e.g., the presynaptic cell, the postsynaptic cell) of a synapse in response to an application of energy. The depicted system includes a pulse generator (as part of a therapy module 12) coupled to an energy application device (e.g., ultrasound transducer(s), such as depicted as part of the probe module 14). The energy application device is configured to receive, e.g., via leads or wireless connection, or otherwise generate energy pulses that in use are directed to a target region in an internal tissue or an organ of a subject, which in turn results in a targeted physiological outcome.

In certain embodiments, the energy application device and/or the pulse generator may communicate wirelessly, for example with a controller that may in turn provide instructions to the pulse generator. As discussed herein, the energy application device may be an extracorporeal device, e.g., may operate to apply energy transdermally or in a noninvasive manner from a position outside of a subject's body, and may, in certain embodiments, be integrated with the pulse generator and/or the controller. In embodiments in which the energy application device is extracorporeal, the energy application device may be operated by a caregiver, or the patient, and positioned at a spot on or above a subject's skin such that the energy pulses are delivered transdermally to a desired internal tissue. Once positioned to apply energy pulses to the desired site, the system 10 may initiate neuromodulation of one or more nerve pathways to achieve a targeted physiological outcome or clinical effect. In some embodiments, the system 10 may be implemented such that some or all of the elements may communicate in a wired or wireless manner with one another.

The system 10 may include an assessment device or logic that assesses characteristics that are indicative of the placement and orientation of the energy application device 14. Based on such an assessment, delivery of therapeutic ultrasonic energy may be altered, modulated, or steered automatically to achieve the prescribed therapeutic result. By way of example, the therapy beam may be electronically steered to the target location when applying a therapy dose. In addition or in the alternative, an indication or guidance may be provided to the user, such as via audible, visible, or haptic indicators, to provide guidance regarding placement and/or orientation of the energy application device 12.

The system 10 as provided herein may provide energy pulses according to various modulation parameters as part of a treatment protocol to apply a prescribed amount of energy. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. Further, the treatment protocol may specify a time of day to apply energy or a time relative to eating or other activity. The treatment duration to cause the targeted physiological outcomes may last for various time periods, including, but not limited to, from a few minutes to several hours. In certain embodiments, treatment duration with a specified stimulation pattern may last for one hour, repeated at, intervals, e.g., 72 hour intervals. In certain embodiments, energy may be delivered at a higher frequency, say every three hours, for shorter durations, for example, 30 minutes. The application of energy, in accordance with modulation parameters, such as the treatment duration, frequency, and amplitude, may be adjustably controlled to achieve a desired result.

With the preceding context in mind, additional features illustrated in FIG. 1 are described in greater detail. In particular, aspects and components of an implementation of the system 10 are shown as modules corresponding to certain functionalities described above. As noted above, the block diagram of FIG. 1 illustrates a therapy module 12 and a probe module 14 which may be used to perform therapeutic functions described herein. An imaging module 16 is also illustrated, though it may be appreciated that in certain embodiments such an imaging module 16 may be absent. In such alternative embodiments analytics performed on imaging data may be performed on unreconstructed (i.e., raw) imaging data or on image data that is reconstructed but not displayed. By way of example, therapy administration and/or control based on data acquired using imaging transducers or at the imaging module 16 may be based on reconstructed images (e.g., signatures within the reconstructed image data) or based on ultrasound signatures present in the unreconstructed image data.

Beginning with the probe module 14, in the depicted example the probe module 14 includes transducers 20. As used herein, a "transducer" refers to any arbitrarily sized and segmented physical structure for converting to and/or from a first energy source (i.e. electrical, mechanical, magnetic, etc.) and ultrasonic energy, where the probe module 14 includes a collection of one or more transducers. As discussed herein, the geometry of the collection of transducers could be a linear (1D) array, a 2D array, or any other suitable geometry of any size, while the imaging and therapy transducers as described herein could be independent, partially shared, or fully shared. In some contexts, the "imaging transducer" or "therapy transducer" may be used to refer to the collection of one or more transducers used for the associated imaging or therapy function. In other contexts, an "imaging beam" or "therapy beam" may be discussed which is generated from a collection of one or more transducers, wherein the collection of transducers used for generating the imaging and therapy beams may be independent, partially shared, or fully shared.

With this in mind, in the depicted example, the transducers 20 include both imaging transducers 22 and therapy transducers 24. In one implementation, the therapy transducer(s) 24 may operate at a frequency within 0.2 MHz to 2 MHz (such as 0.5 MHz or 2 MHz). The probe module 14 and/or transducer(s) 20 may be selectable or swappable in certain implementations to allow a clinician to choose an appropriate probe module model or type to best fit the patient or target region context, such as by allowing the clinician to select the probe module 14 and/or transducer(s) 20 having suitable nominal depth, axial focus location characteristics, power handling, frequency range, angular adjustment, attenuation adjustment, and so forth. Further, in multi-transducer embodiments, a clinician may customize the probe module 14 by selecting the subset of transducers for activation to enable coherent summation of a therapy beam at a target region of anatomy with minimal interference by obstructing anatomic structures (e.g., ribs, and so forth).

In alternative embodiments, transducers 20 may instead comprise one type of transducer capable of operating at both the respective imaging and therapy frequencies (e.g., 0.2 MHz to 2 MHz during therapy operation and 2 MHz to 12 MHz during imaging operation) such that separate transducers are not provided for each type of respective operation. In such embodiments the single transducer or type of transducer may be operated to both provide therapy and acquire imaging-type data. Such single transducer type approaches may be suitable in contexts where the target region is shallow and/or high power is not necessitated. The probe module 14 and/or transducer(s) 20 may be selectable or swappable in certain implementations to allow a clinician to choose an appropriate probe module model or type to best fit the patient or target region context, such as by allowing the clinician to select the probe module 14 and/or transducer(s) 20 having suitable nominal depth, axial focus location characteristics, power handling, frequency range, angular adjustment, attenuation adjustment, and so forth.

In the depicted example the probe module 14 also includes a hardware controller 30 which in the depicted example, includes a microcontroller(s) (MCU) 32 in communication with a master controller (e.g., processor) 80 of the therapy module 12 and a field-programmable gate array (FPGA) 34 in communication with the MCU 32 and sensors 40 and/or actuators 50 that may be present and associated with the probe module 14. In this configuration the MCU 32 and FPGA 34 may bi-directionally communicate with components of the master controller 80 to coordinate and/or record operation of aspects of the probe module 14 or, if present, components associated directly or indirectly with the probe module 14, such as actuators 50 and/or sensors 40. With respect to the sensors 40, various types of sensors may be integrated with or, if separate, in communication with the probe module 14. By way of example the sensors 40 may include one or more of inertial measurement units (IMUs) (which may function as posture sensors), a contact force sensor, a tension or strain sensor, and so forth. As shown in FIG. 1, the one or more sensors 40, if present, may be communicatively coupled to the FPGA 34 or otherwise to the hardware controller 30.

Regarding the therapy module 12, as previously noted implementations of the therapy module 12 may include a master controller (e.g., processor) 80 which may itself include or execute various sub-modules or routines, such as may be stored on a memory structure 84. For example, the master controller 80 may include or execute modules or routines providing functionality for an image streamer and remote control, artificial intelligence (AI) anatomy recognition and tracking, a guided dosing engine, a user interface, support analytics, a data logger and so forth.

As with the probe module 14, in certain embodiments the therapy module 12 may include a hardware controller 86 which may include its own MCU 88 and FPGA 90. While depicted as separate modules for the purpose of illustration and explanation, in practice the probe module 14 and therapy module 12 may actually be one and the same (i.e., an integral structure or device configured to perform the functions of both the therapy module and probe module as discussed herein). With this in mind, though discussed separately herein, in practice the hardware controllers 30 and 86 may be implemented as a single hardware controller. In the depicted example the MCU 88 is depicted as being in communication with the master controller 80 and its components and modules. The FPGA 90 communicates with and/or controls other components of the therapy module 12, such as therapy pulser-receivers 92 (depicted as being in communication with the therapy transducers 24 of the probe module 14), safety circuitry 94, and/or power management circuitry 96. In practice, the master controller 80 in conjunction with the hardware controllers 86, 30 may control operation of the therapy module 12 and probe module 14, such as to perform application of therapy in accordance with processes and structures described herein. In addition, as shown in FIG. 1, one or both of the master controller 80 and/or hardware controller 86 may be in communication with one or more memory structures 84 (e.g., a volatile or non-volatile memory, a firmware construct, a mass data storage, and so forth). As may be appreciated code or executable routines for performing operations (e.g., therapy procedures or protocols) may be stored on the memory 84 for use by other components. In addition, one or more configurable parameters (e.g., system settings, imager settings, sensor settings or thresholds, and so forth) may be stored in the memory structure 84, such as by a user who has configured or calibrated the system 10 for use by a given patient for a respective therapy protocol. In addition, the memory structure 84 may be used to store data (e.g., image data) acquired or generated as part of a therapy procedure, such as for later readout and evaluation.

In the depicted example, an imaging module 16 is also depicted as being a component of the overall system. Such a module, if present, may control or monitor operation of transducers 20 (e.g., imaging transducers 22) to control generation, collection, and/or processing (e.g., reconstruction) of imaging data. In the depicted example, the imaging module 16 is also shown as being in communication with the master controller 80 of the therapy module 12, which may control operation of or respond to feedback and data from the imaging module 16. As with the probe module 14 and therapy module 12 discussed above, the imaging module 16 is illustrated as a separate module in FIG. 1 to facilitate illustration and explanation of the functional concepts. However, as with the preceding examples, the imaging module 16 may actually be one and the same with one or both of the probe module 14 and therapy module 12 (i.e., an integral structure or device configured to perform the combined functions of the imaging module and one or both of the therapy module and probe module as discussed herein).

With the preceding system description in mind and as context, the present techniques relate to an image (or unreconstructed image data) guided ultrasonic therapy system. In certain embodiments, a device or structure to provide targeting and/or alignment assistance without manual guidance is used in conjunction with the system 10 discussed with respect to FIG. 1. Such targeting and alignment devices may include customizable elements and/or may be otherwise personalized for each patient's unique external body shape and size and to the patient's internal anatomy shape, size, and location. The systems and devices are customizable to address the large variability in the overall patient population, while also being suitable for use in non-clinical settings (e.g., home use by the patient).

A variety of example embodiments of targeting and alignment devices, referred to herein collectively as probe positioning structures, are described herein. These devices may, when used, facilitate the application of safe and effective ultrasound neuromodulation therapy, including in non-clinical settings and/or when operated by untrained users (e.g., the patient themselves or other individuals lacking clinical or medical training). As such certain of the presently described embodiments are designed or configured for ease of use by the end user.

By way of context, in conventional ultrasound scans there is a high-degree of variability across the patient population. A trained sonographer adapts to such patient variability by adjusting the probe placement location on the body, probe angles, and system settings to arrive at a diagnostic image of the target. As noted herein, the present probe positioning structures help avoid such manual operations (thereby facilitating placement and use by an untrained individual) to allow personalized, easy, and repeatable probe positioning and hands-free operation during a therapy session.

Figure 2:
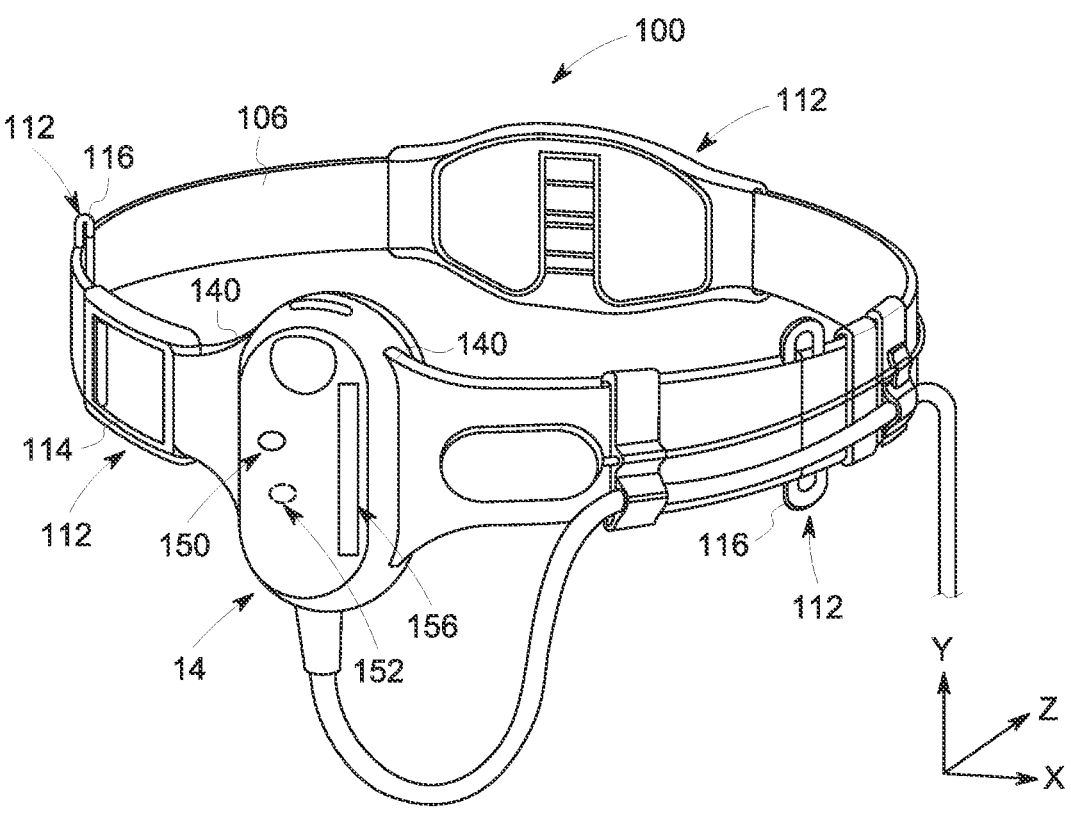
FIG. 2 depicts a wearable structure suitable for use as an ultrasound probe positioning structure, in accordance with aspects of the present disclosure.

With this in mind, in a first example of an implementation of a probe positioning device in the form of a wearable structure 100, as shown in FIG. 2, a body-worn, adjustable probe positioning structure is depicted that is suitable for hands-free use (i.e., neither the device nor the affixed probe need to be held during operation). In this example the probe positioning structure may be provided as a wearable belt 106 (shown), vest, harness, etc., although other wearable devices or rigs (suitable for the appropriate body location) may also be employed. With this in mind, the probe positioning structure in this embodiment may comprise a body-worn, hands-free (i.e., the user does not hold either the wearable structure 100 or the probe module in place using their hands) fixture that is at least initially adjustable (i.e., on the first use or through a calibrating or fitting operation). In the depicted example of a belt 106 the user may put on the belt 106 and adjust or fit the belt 106, such as by adjusting one or more fitting features 112 provided on the wearable structure 100 (e.g., tightening or loosening one or more straps or other adjustable features). Once worn and fitted in this manner, the belt 106 (or comparable wearable structure 100) may be worn and used in a hands-free manner for the duration of a therapy or treatment session.

The one or more fitting features 112 may include, but are not limited to, tightening and/or cinching features like clips 114, locks, adjustable straps 116, ratchets, pull cords, lace tensioning systems, or inflatable features. Such tightening and/or loosening features may be either manual (i.e., user operated or adjusted) or automated (e.g., automatically adjusted utilizing a motorized mechanism in response to sensor and/or image data) as discussed herein. With respect to fit of the wearable structure 100, the wearable structure 100 may be provided in multiple sizes (e.g., small, medium, large, extra-large) and the closest size selected for a patient prior to adjustment. Alternatively, the wearable structure 100 may be provided in a single size (i.e., one size fits all) and the fitting features 112 relied upon solely to adjust or adapt the fit of the probe positioning structure to each patient.

In FIG. 2, a probe 14 (e.g., a central dual-mode imaging/therapy ultrasound probe) is illustrated as attached to a coupling structure or feature 140 (e.g., a probe clip or connector) of the wearable structure 100. It may be noted that other probe configurations (e.g., non-central and/or multi-transducer configurations) connected to or positioned on the wearable structure 100 are also possible.

One or both of the wearable structure 100 or the probe 14 may include sensors that may be used to measure and guide fitting of the wearable structure 100. By way of example, the probe 14 and/or wearable structure 100 may include an inertial measurement unit (IMU) 150 as a posture sensor. Such an IMU 150 may be embedded within the probe 14 and may be employed in a fitting session to measure device (e.g., probe) orientation (which may correspond to a patient posture) that is suitable for a treatment or therapy session. Measurements from the IMU 150 may then be used in a dosing or treatment session to ensure the posture of the patient corresponds to what is anticipated based on the fitting session. By way of further example, a contact force sensor 152 may also be provided, such as on a patient-facing surface of the probe 14. In such an example, the contact force sensor 152 may be used in a fitting session to measure contact force between the probe 14 and patient, thereby obtaining a measurement or guidance for adjustment in the Z-dimension in the direction running from the probe face into (i.e., toward) the patient. Measurements from the contact force sensor 152 may then be used in a dosing or treatment session to ensure proper contact force is present before the dose is applied. By way of an additional example, a tension or strain sensor 156 may also be provided, such as at a connection point on the belt 106. In such an example, the tension sensor 156 may be used in a fitting session to measure tension baseline belt tension when the belt 106 (or other wearable structure 100) is properly fitted to the patient. Measurements from the tension sensor 156 may then be used in a dosing or treatment session to ensure proper tensioning before the dose is applied.

Figure 3:
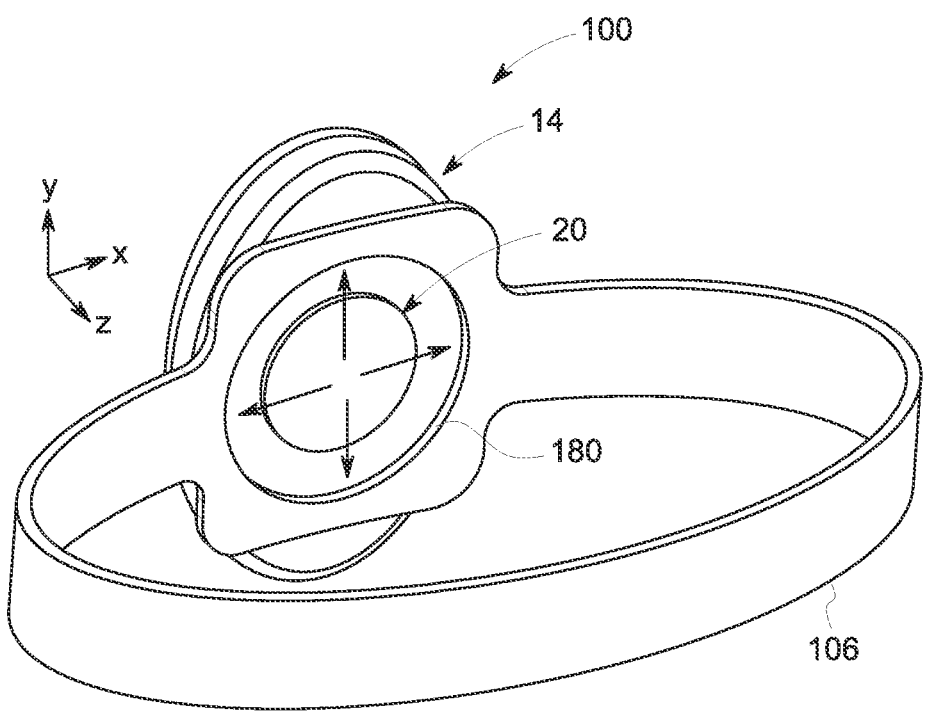
FIG. 3 depicts a further view of a wearable structure suitable for use as an ultrasound probe positioning structure, in accordance with aspects of the present disclosure.

Turning to FIG. 3, a further example of a wearable structure 100 in the form of a belt 106 is provided for the purpose of illustrating a contemplated manual adjustment mechanism in x-, and y-dimensions (i.e., along the surface of the patient in vertical and horizontal directions, as opposed to toward the patient in the z-dimension). In this example, the belt 106 may be fitted to the patient using a mechanism as described with respect to FIG. 1. A probe 14 having patient-facing transducer(s) 20 is provided on the belt 106 either as an integral feature of the belt 106 or a mountable (e.g., clippable) attachment. For example, as noted herein, the probe 14 (may be a central dual-mode imaging/therapy ultrasound probe) and may attach to a coupling feature (e.g., a probe clip or connector) of the wearable structure 100, here belt 106. In FIG. 3, the belt 106 is shown from a perspective view in which the patient-facing surface of the probe 14 is visible through an acoustic window 180 provided in the belt 106.

In one implementation utilizing the wearable structure 100 as shown in FIG. 3, the belt 106 may be applied to the patient and the probe 14, and associated transducer(s) 20 can be moved in the x-, y-dimensions relative to the acoustic window 180 of the belt 106 to achieve placement of the probe 14. In certain such embodiments, the user may adjust the position of the transducer(s) 20 by moving the probe 14 in the x- and y-dimensions relative to the acoustic window 180 while the system 10 analyzes concurrently acquired ultrasound image data. In one embodiment, the system 10 guides the user (e.g., using optical, audible, and/or haptic feedback or cues) to move the probe 14 in the x- and y-dimensions relative to the acoustic window 180 to obtain alignment with the target region. Alternatively, in another implementation the user randomly moves the probe 14, and associated transducer(s) 20 within the acoustic window 180 until the system 10 indicates that alignment with the target region has been achieved. The indication may be a binary yes/no, or the system 10 may guide during the random motion using optical, auditory, and/or haptic cues or feedback (e.g., by beeping faster or louder (or similar visual feedback) as the user gets closer to the aligned position).

As in the example discussed with respect to FIG. 2, the belt 106 of FIG. 3 may also be fitted with sensors 40 that may be used to measure and guide fitting of the belt 106. By way of example, sensors 40 may be employed to measure and/or provide feedback with respect to belt tightness, contact force, posture, and/or body position.

In further embodiments the belt 106 may not allow or may limit adjustment of the transducer(s) 20 in the x-, y-dimensions subsequent to the belt 106 being fixed in place. In such embodiments, the x-, y-alignment of the transducer(s) 20 may be done prior to locking down (i.e., securing) the belt 106 for a therapy session. For example, the user (e.g., patient) may place the belt 106 (or other positioning device) in the appropriate general position on the patient (e.g., without tightening or locking the belt 106 in position). The user may then shift or adjust the placement of the probe 14 or the wearable structure 100 (e.g., belt 106) with the probe 14 attached until alignment with the target region is achieved, such as via a feedback or notification mechanism as described above. Once alignment with the target region is obtained, the user (e.g., patient) may tighten or secure the wearable structure 100 to lock the probe 14 into position for the therapy session.

In another implementation, the wearable structure 100, such as the belt 106, may include a locking mechanism (e.g., a quick locking mechanism) that the clinician may utilize during a fitting session to lock or fix the position and orientation of the probe 14 once the proper position and orientation are determined and once the probe is re-engaged or attached to the belt 106. In such an embodiment, the locking mechanism prevents or limits, once locked, manipulation or adjustment of the probe position and orientation settings specified by the clinician, even when the probe 14 has been disengaged or removed (e.g., unclipped) from the probe positioning structure 100, such as when not in use. In this manner, a non-clinician user may be prevented or limited in their ability to reposition or reorient the probe 14 when attached to the wearable structure 100 after the fitting process.

In one such example, during an initial fitting or calibration session a clinician manually adjusts the fit of the belt 106 and the probe 14 coupled to the belt 106 relative to the acoustic window 180 to align the transducer(s) 20 of the probe 14 with the target region. During fitting, the clinician may also adjust the fit of the probe 14 in the z-dimension for optimal probe placement with respect to the target region and to ensure good acoustic contact with the patient when fit. The fitting session may also fix the orientation of the probe 14 (as opposed to the x-, y-, and z-dimension positioning of the probe) when affixed to the belt 106, such as by adjusting one or more of roll, pitch, or yaw (e.g., rock, tilt, spin, and so forth) of the probe 14 when affixed to the belt 106 so as to be calibrated or locked to a suitable (e.g., optimal) scan plane with respect to the target region. Once the position and orientation of the probe 14 are so determined such as to align with the target region, the locking mechanism may be set or locked so that the probe 14, when coupled to the wearable structure 100 is aligned with the target region when the wearable structure 100 is applied to the patient and secured.

In this manner, once the wearable structure 100 and probe 14 are fitted for subsequent therapy sessions, the user (e.g., patient) may apply the wearable structure 100 and probe 14 during a therapy session such that the probe 14 is properly positioned and oriented to apply therapy. In certain embodiments, the user may be allowed a limited ability adjust the position of the transducer(s) 20 by moving the probe 14 in the x-, y-, and/or z-dimensions relative to the acoustic window 180 to a limited extent while the system 10 analyzes concurrently acquired ultrasound image data. That is, in some implementations the range over which the user may make adjustments to the position and/or orientation of the affixed probe 14 may be limited in scope if a lockout mechanism is employed, essentially allowing a user the ability to fine tune or optimize the position and orientation of the probe 14 within the limits set by the locking mechanism. In one embodiment, the system 10 guides the user (e.g., using optical, audible, and/or haptic feedback or cues) to move the probe 14 in the x- and y-dimensions relative to the acoustic window 180 to obtain final alignment with the target region.

Figure 4:
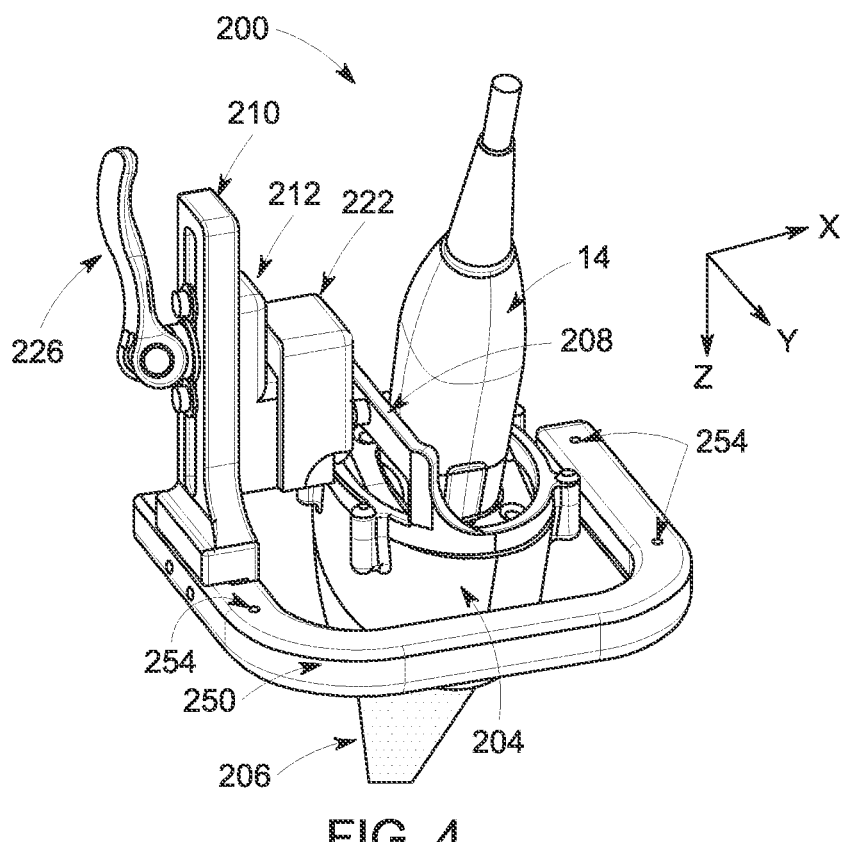
FIG. 4 depicts an example of a probe holder for use with an ultrasound probe positioning structure, in accordance with aspects of the present disclosure.

While the preceding discussion relates various aspects of a generalized probe placement device design and associated fitting concepts, various illustrative design and use examples will be provided below to illustrate real-world or practical implementations or aspects of such approaches. By way of example, and turning to FIGS. 4 (an external view) and 5 (a corresponding cut-away view), an example of one implementation of a probe holder 200 suitable for coupling to a wearable structure 100 (such as at acoustic window 180 and using coupling features 140) is illustrated. The depicted example of a probe holder 200 may allow for manual adjustments (such as by a clinician performing an initial fitting or calibration or by a non-clinical user) with respect to the x- and y-dimensions (i.e., the x- and y-positioning within the acoustic window 180 of a wearable structure 100 and/or placement of the wearable structure 100 itself) as well as with respect to the z-dimension orthogonal to the patient skin surface and/or the angle or tilt of the probe 14 (i.e., angular adjustment). In addition, the example implementation depicted provides a locking mechanism to lock both the z-axis positioning, angular positioning, and so forth once fitted to the patient.

Figure 5:
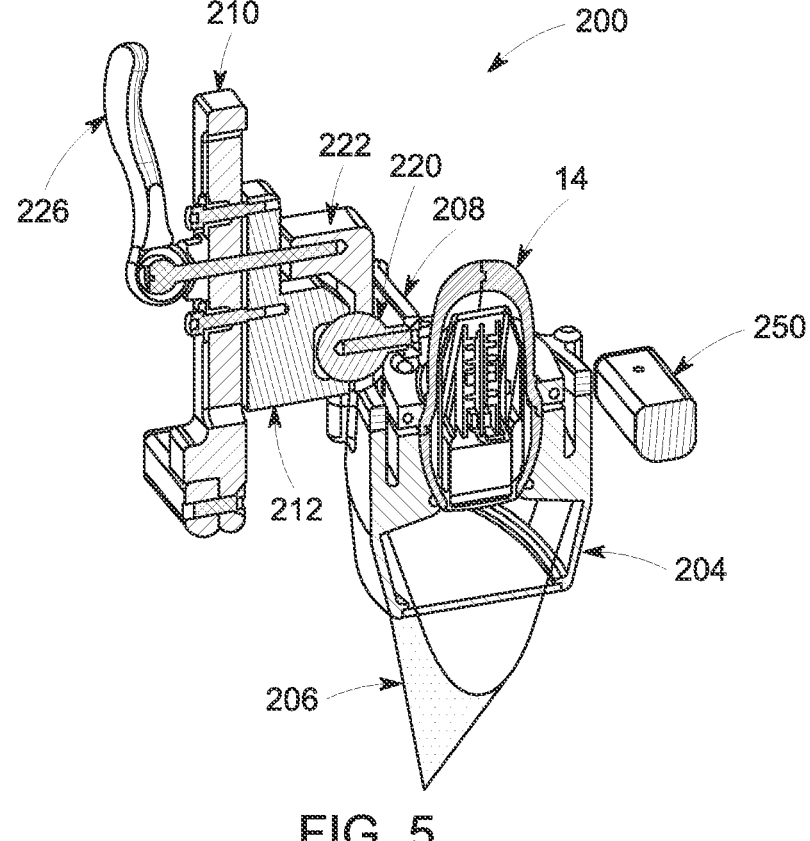
FIG. 5 depicts a cut-away view of the probe holder of FIG. 4, in accordance with aspects of the present disclosure.

The probe carriage frame 208 is connected to a z-axis rail 210 via a z-axis carriage 212 so as to allow the probe module 14, when attached to the probe carriage frame 208 to be moved in the z-dimension (i.e., toward or away from the patient). As shown more clearly in the cut-away view of FIG. 5, a spherical joint 220 is also provided which resides partially within an indent of the z-axis carriage 212 and connects to the probe carriage frame 208. In this example, the spherical joint 220 allows the probe carriage frame 208 (and attached probe module 14) to rock, tilt, and/or spin based on the range of motion provided by the spherical joint 220.

A spherical joint clamp 222 is provided that secures the spherical joint 220 with respect to the z-axis carriage. In the depicted example, the spherical joint clamp 222 is connected to a clamp lever 226 that may be manually actuated between a locked and unlocked position. In the depicted example, the clamp lever 226 is illustrated along the side of the z-axis rail 210 and is coupled to an extension that passes through the z-axis rail 210 and z-axis carriage 212 to engage with the spherical joint clamp 222. By moving the clamp lever 226 from the unlocked to locked position, a user may simultaneously lock movement of the z-axis carriage 212 and the spherical joint 220 so as to lock the probe carriage frame in the z-dimension and in the spin, rock, and tilt orientations.

With respect to focus in the z-dimension, while the movement and securing of the probe module 14 in the z-dimension is one approach to achieving the proper focal plane, it should also be appreciated that selection of a suitable probe module 14 from among a set of available probe modules may also be part of achieving suitable z-focus. By way of example, a set of available probe modules having suitable therapy transducers (e.g., single element transducers) may each have a different respective intrinsic z-dimension focus (e.g., 6 cm, 8 cm, 10 cm, and so forth), as represented by therapy beam cone 206. At a fitting session a clinician may select a probe module 14 from the set of available probe modules that best matches the depth of the target region for the respective patient. The selected probe module having an intrinsic z-focus may be paired with the probe holder 200 for fitting and/or calibration.

Figure 6:
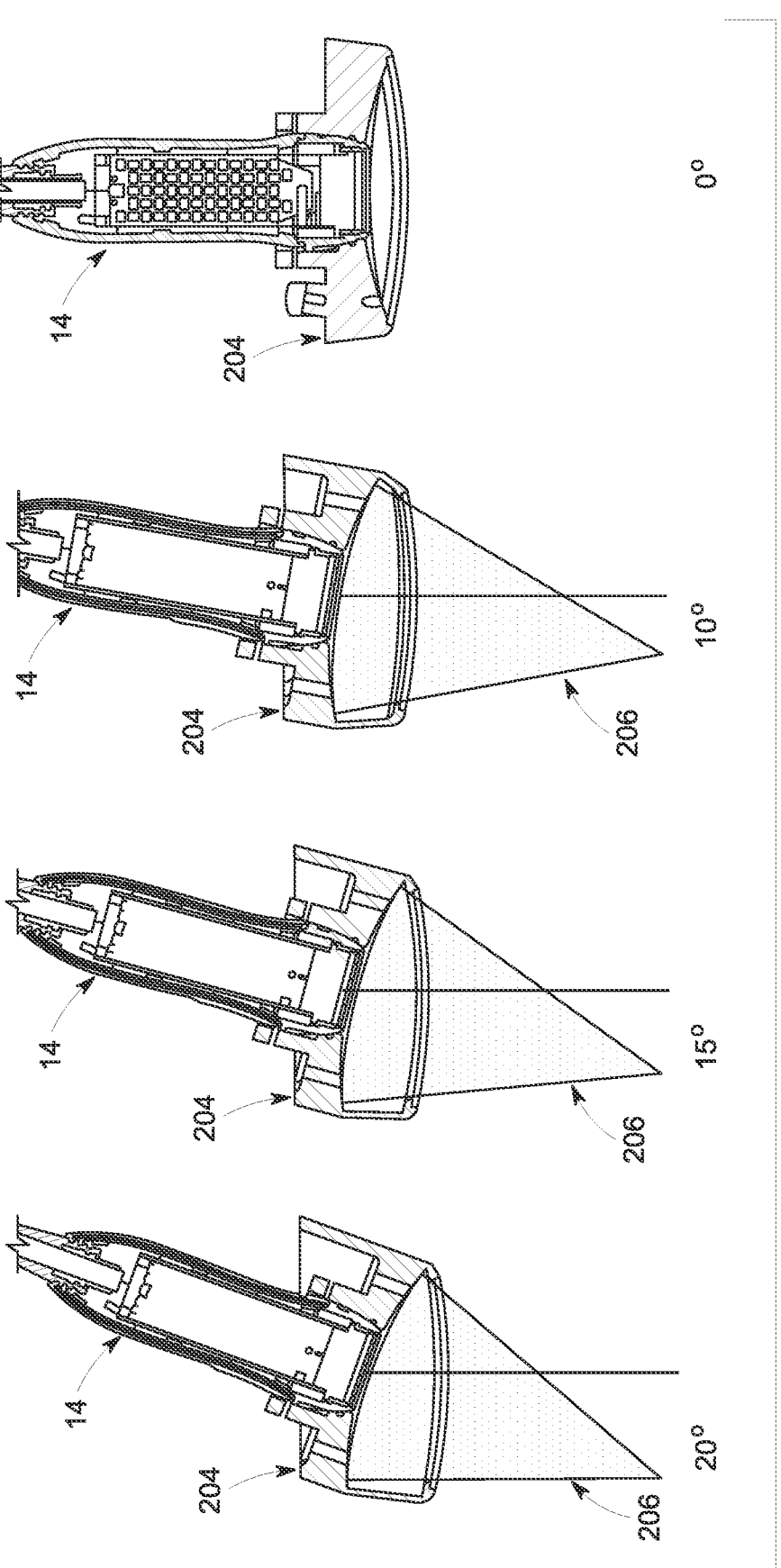
FIG. 6 depicts examples of probe caps for use with an ultrasound probe positioning structure, in accordance with aspects of the present disclosure.

In addition, the respective probe modules 14 from the available set may also (or instead) differ with respect to angle or orientation of the probe module 14 with respect to the patient. As shown in FIG. 6, the angular orientation of the respective probe modules 14 with respect to the patient (i.e., to direct the focal beam to the correct x-position corresponding to the target region within the focal plane) may be determined by a probe cap 204 with which the probe modules 14 are affixed. Such probe caps 204 may be permanently affixed to the probe modules 14 or may be removable and interchangeable. Different probe caps 204 may be associated with a different respective angular orientation (e.g., −20°, −10°, 0°, 10°, 20°, and so forth) such that selection of a probe cap 204 determines the angular orientation of the probe module 14 with respect to the patient once affixed to the probe holder 200. By way of example, a swappable probe cap may adapt the angle at which the probe module 14 contacts the body surface so as to reduce the rock or tilt angles on the body surface or size of the acoustic aperture to best fit the access zone and anatomical target for the patient. In addition to or in the alternative of this angular adjustment, probe caps 204 may also be distinguished by and selected based on attenuation characteristics or adjustment (e.g., standoff height, standoff composition, and so forth), geometry and/or focusing features useful for focusing, shaping or otherwise targeting the beam), and so forth.

Turning back to FIGS. 4 and 5, the probe holder 200 includes a frame 250 which functions as an attachment interface to a belt, vest, or other positioning structure so as to form the probe positioning aggregate structure. In this example, the z-axis rail 210 attaches to the frame 250 (such as via rail mount points) so as to attach the components connected to the z-axis rail 210 (e.g., the remainder of the probe holder 200) to the frame 250. In this example, the frame 250 includes attachment points 254 (e.g., belt rail mount points) that may engage with a complementary structure (e.g., an anchor point or attachment rail) on a positioning device, such as a belt. For example, the attachment points 254 on the frame 250 may engage or secure to complementary attachment points on an attachment rail provided on a belt or vest of a probe positioning structure.

With the preceding discussion in mind of a probe holder 200 that may be suitable for incorporation with a wearable structure 100, as generally discussed within, the following three examples illustrate different approaches for implementing a probe positioning structure. It should be appreciated that the following examples are merely illustrative of different concepts and are not intended to limit the manner in which a probe positioning structure may be provided. Instead, the following example are merely intended to provide context and a real-world framework to better illustrate and explain how such a probe positioning structure might be implemented and employed. As may be appreciated, to the extent that the various wearable structure 100 implementations discussed herein are of a suitable size and/or flexibility, such probe positioning structures may be configured to fit in or be otherwise stored in a compartment in a therapy module 12 for use with the probe module 14. In this manner, the wearable structure 100 may be conveniently stored with the devices with which it is to be used.

Figure 7:
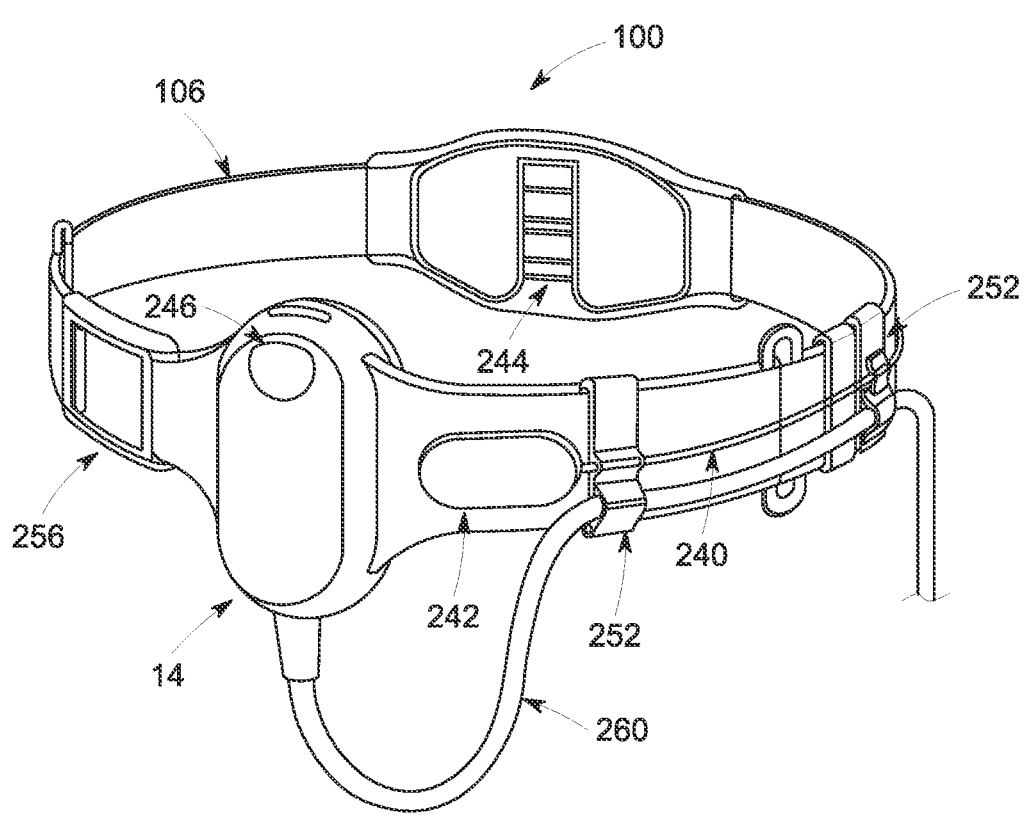
FIG. 7 depicts a wearable structure suitable for use as an ultrasound probe positioning structure, in accordance with aspects of the present disclosure.
Figure 8:
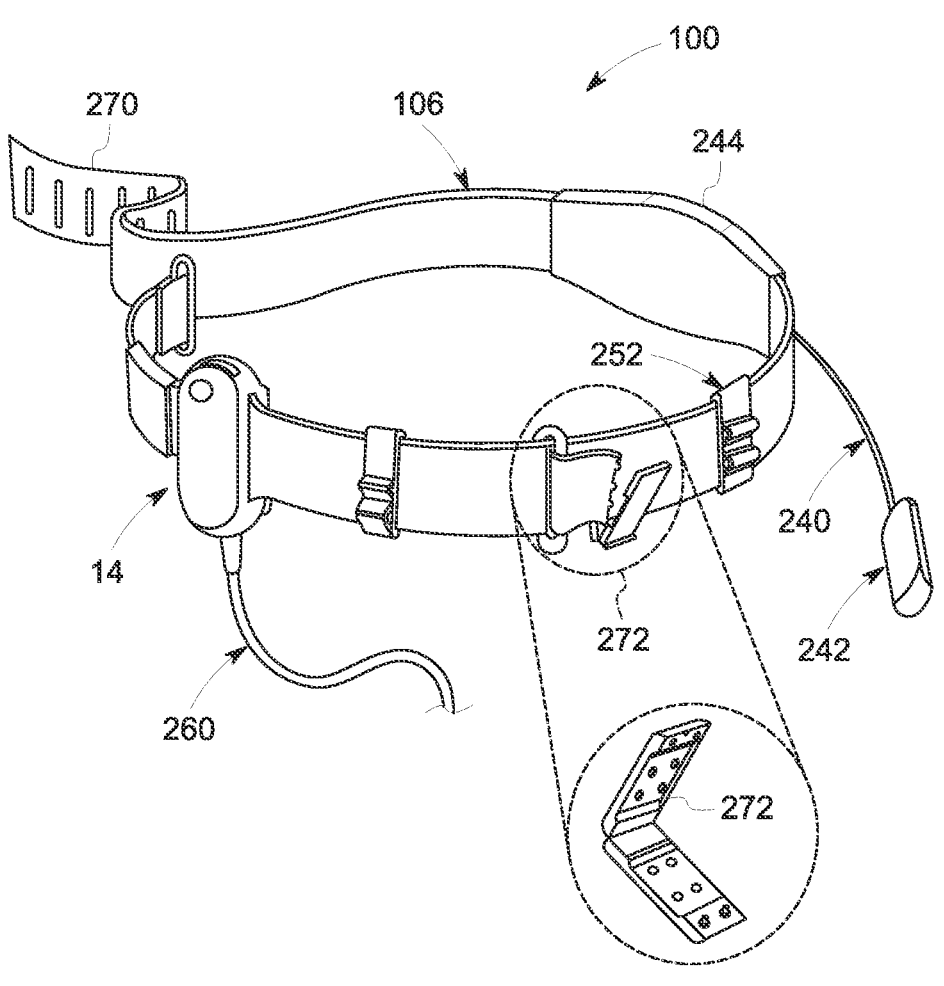
FIG. 8 depicts a wearable structure suitable for use as an ultrasound probe positioning structure, in accordance with aspects of the present disclosure.

Turning to FIGS. 7 and 8, a wearable structure 100 in the form of a belt 106 is illustrated that has one or more tensioning features and which is easy to put on and remove. In one embodiment, the belt 106 may be a "one size fits all" belt that is customizable or configurable to fit different body sizes or weights. For example, the implementation shown in FIG. 7, and with certain fitting and/or adjustment features highlighted in FIGS. 8 and 9, may be initially configured or fit in a fitting session and later applied by a clinician or by a non-clinician for therapy sessions. As may be appreciated, in practice the belt 106 may be oriented or positioned to hold the probe module 14 in a clinically relevant position and orientation and thus the probe module 14 may be held on the front, back or side of the patient. In certain embodiments, for ease of use by a non-clinician, the probe module 14 may include a power on/off button or switch 246 of an outward facing surface for easy activation.

By way of example, the belt 106 may be secured and released via a magnetic closure 256 that is easy and quick to operate. Adjustments may be accomplished using a pull-string lace tightening system, which is illustrated in FIGS. 7 and 8 and including a pull string 240 having a pull handle 242 and which controls the separation provided by one or more lace or webbing portions 244 of the belt 106, thereby allowing tightening or loosening of the belt 106. By way of example, during a fitting session, the belt 106 may be secured, such as via magnetic closure 256, and once secured, the pull handle 242 tightened to cause the belt 106 to fit the patient in a manner that placed the probe module 14 in the appropriate location and orientation. The pull string 240 and pull handle 242 may then be secured by cable or cord fastening features 252 so as to prevent adjustment to the fit. The cable fastening features 252 may also be used to secure other cables or strings, such as a probe module cable 260 running between a therapy module and the probe module 14.

In certain embodiments, the probe module 14 may be configured to communicate with the therapy module or a consumer electronic device (e.g., an application running on a cellular telephone of the patient) to facilitate electronic troubleshooting or alignment. By way of example, once the fitted belt 106 and probe module 14 are applied to the patient, the patient may utilize an application on a cellular telephone to perform an automatic adjust or alignment process that may electronically align and steer the therapy beam so as to address small misalignments.

Aspects of this adjustable system are illustrated in FIG. 8, along with other aspects that may facilitate adjustment and/or fitting to a patient. For example, in FIG. 8 the pull handle 242 and pull string 240 are shown in an operable configuration such that pulling the pull handle 242 will tighten the webbing portion 244. In addition, the belt 106 is shown as being trimmable to remove excess length 270, such as during a fitting operation. For example, in an implementation where the belt 106 is "one size fits all", the belt, 106, when fitted, may include an excess length 270 that can be cut and removed by the clinician performing the fitting operation. A clip 272 be secured to the belt to secure the end and cover the cut edge, if present.

Figure 9:
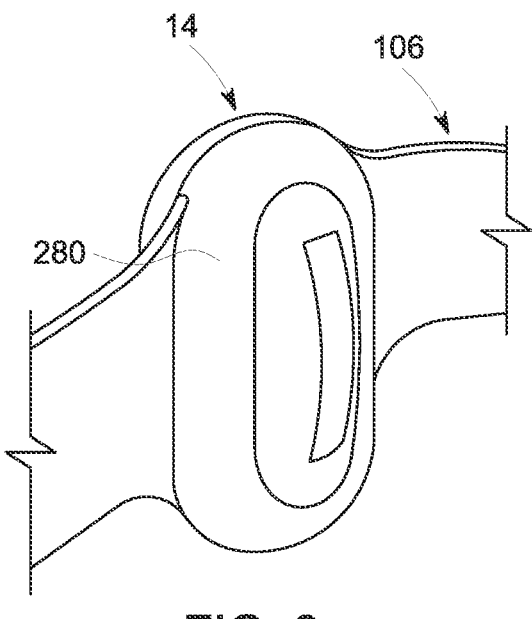
FIG. 9 depicts a probe module having surface features and suitable for use with an ultrasound probe positioning structure, in accordance with aspects of the present disclosure.

Turning to FIG. 9, in a further refinement, the probe module 14 may include non-slip protrusions (e.g., bumps, bumpers, "feet") on the patient facing surface so as to limit or eliminate sliding once the probe module 14 is positioned against the patient. By way of example, the protrusions may press into the patient to suppress movement of the probe module 14 when the fitted belt 106 is applied to the patient.

Figure 10:
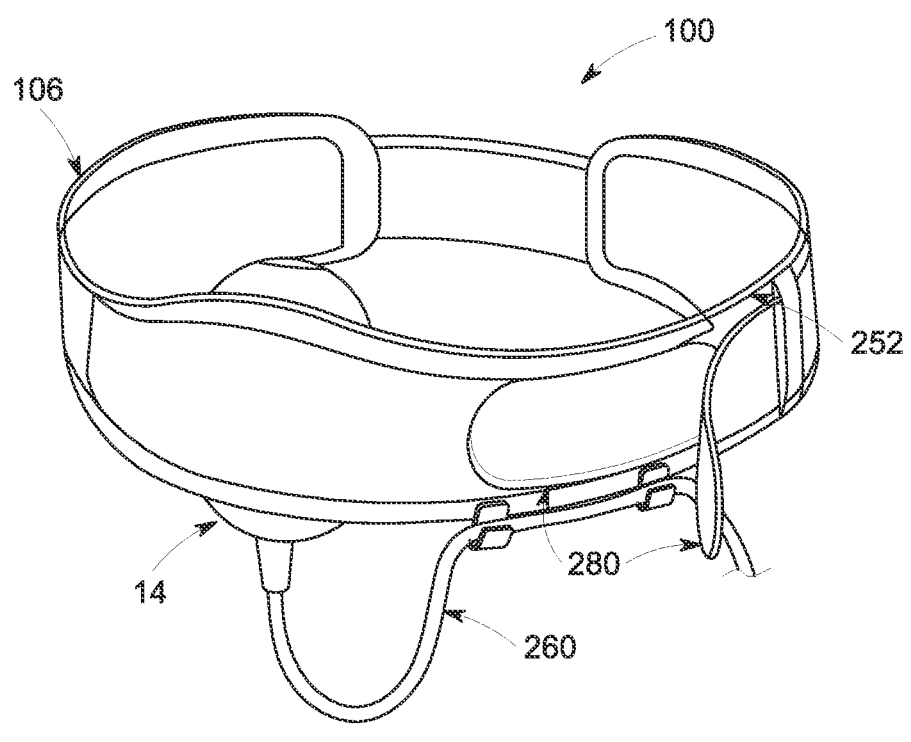
FIG. 10 depicts a wearable structure suitable for use as an ultrasound probe positioning structure, in accordance with aspects of the present disclosure.
Figure 11:
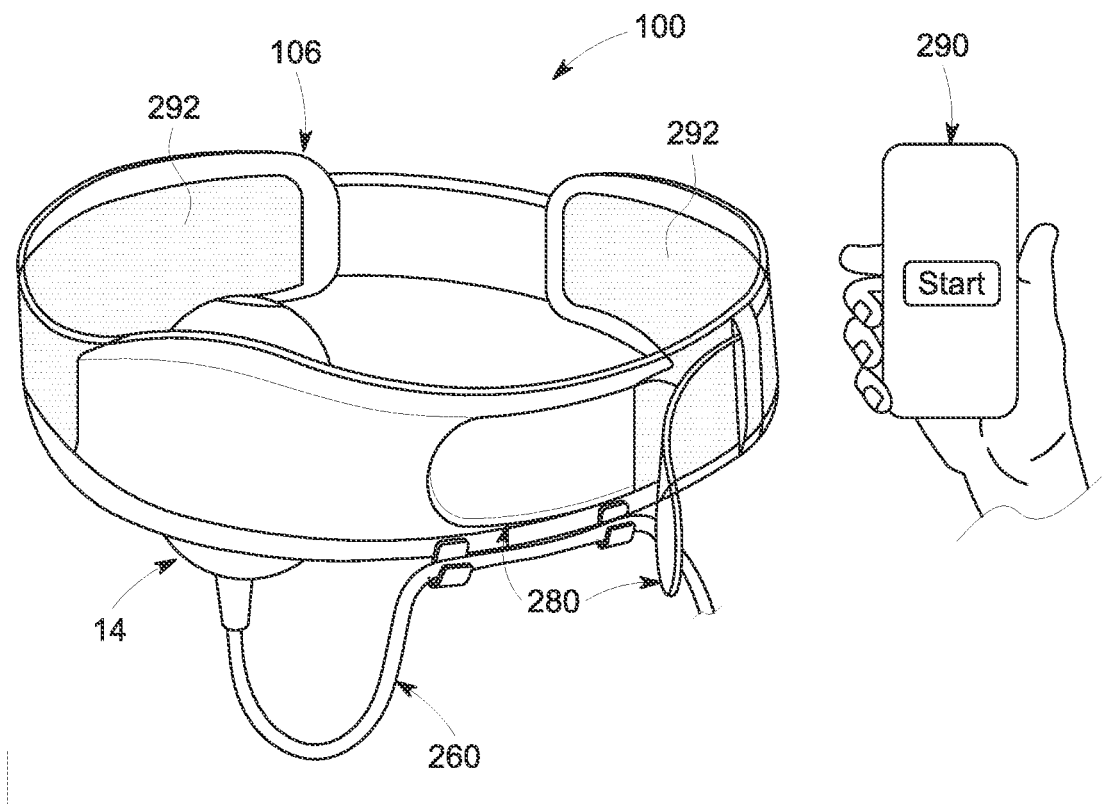
FIG. 11 depicts a wearable structure suitable for use as an ultrasound probe positioning structure, in accordance with aspects of the present disclosure.

Turning to FIGS. 10 and 11, an example of a wearable structure 100 in the form of a belt 106 is illustrated that employs automated tensioning. As in the preceding example, the belt 106 may be a "one size fits all" belt that may fit different body sizes or may come in a limited number of adjustable sizes that can be fit to different body sizes (e.g., one, two, or three sizes). An automated tensioning process, as discussed in greater detail below, may be employed to fit the belt 106 to the patient once applied. As may be appreciated, in practice the belt 106 may be oriented or positioned to hold the probe module 14 in a clinically relevant position and orientation and thus the probe module 14 may be held on the front, back or side of the patient.

In the depicted example, the belt 106 may be applied or fitted to the patient using hook-and-loop fastening system 280 along one side, though other fastening mechanisms may also be employed as appropriate. Once applied to the patient, an automated process may be employed to operate an inflatable cinching system integrated with the belt 106 to a pre-defined tension against the patient. The pre-defined tension may be configured or set by a clinician as part of an initial fitting process and/or may otherwise pre-defined based on standardized tension parameters. As part of the tensioning process, one or more sensors (e.g., a contact force sensor, a tension or strain sensor) provided in one or both of the probe module 14 or wearable structure 100 (e.g., belt 106) may be used to provide strain or force measurements to a processor-based device executing the automated tensioning process. By way of example, the processor-based device may be the therapy module 12, the probe module 14, or a separate device, such as a computer, tablet, or cellular telephone 290, as shown in FIG. 11 and discussed below.

Turning to FIG. 11, internal structural components 292, such as spring steel components (shown by shading) of the belt 106 may be provided that maintain a rounded (e.g., circular or oval) shape to the belt 106 and which may facilitate putting the belt 106 on and taking it off. For example, such structural components 292 help maintain the shape of the belt 106 and may be easily separated to apply or remove the belt 106.

In addition, the belt 106 may include air bladders or other inflatable portions that may be inflated to varying degrees to achieve a prescribed or defined fit to the patient (based on contact force or tension). For example, as noted above, one or more sensors (e.g., a contact force sensor, a tension or strain sensor) provided in one or both of the probe module 14 or wearable structure 100 (e.g., belt 106) may be used to provide strain or force measurements in a real-time manner to an executable tensioning routine controlling inflation of the inflatable portions such that the tensioning routine continues to inflate the inflatable portions until a prescribe tension or contact force is reached. Once the prescribe tension or contact force is reached, the probe module 14 may be further aligned electronically (if necessary) and therapy administered.

In the depicted example, a processor-based device in the form of a cellular telephone 290 is illustrated which may implement or otherwise control operation of the tensioning routine and of the probe module 14 and/or therapy module 12. For example, the cellular telephone 290 may store and execute an application that may start and control inflation of the belt 106 and/or start the therapy session once inflation is completed. In addition, between the steps of inflating the belt 106 and applying the therapy, processes executing on the cellular telephone 290 (or otherwise controlled by cellular telephone 290) may perform an automatic adjust or alignment process that may electronically align and steer the therapy beam so as to address small misalignments.

Figure 12:
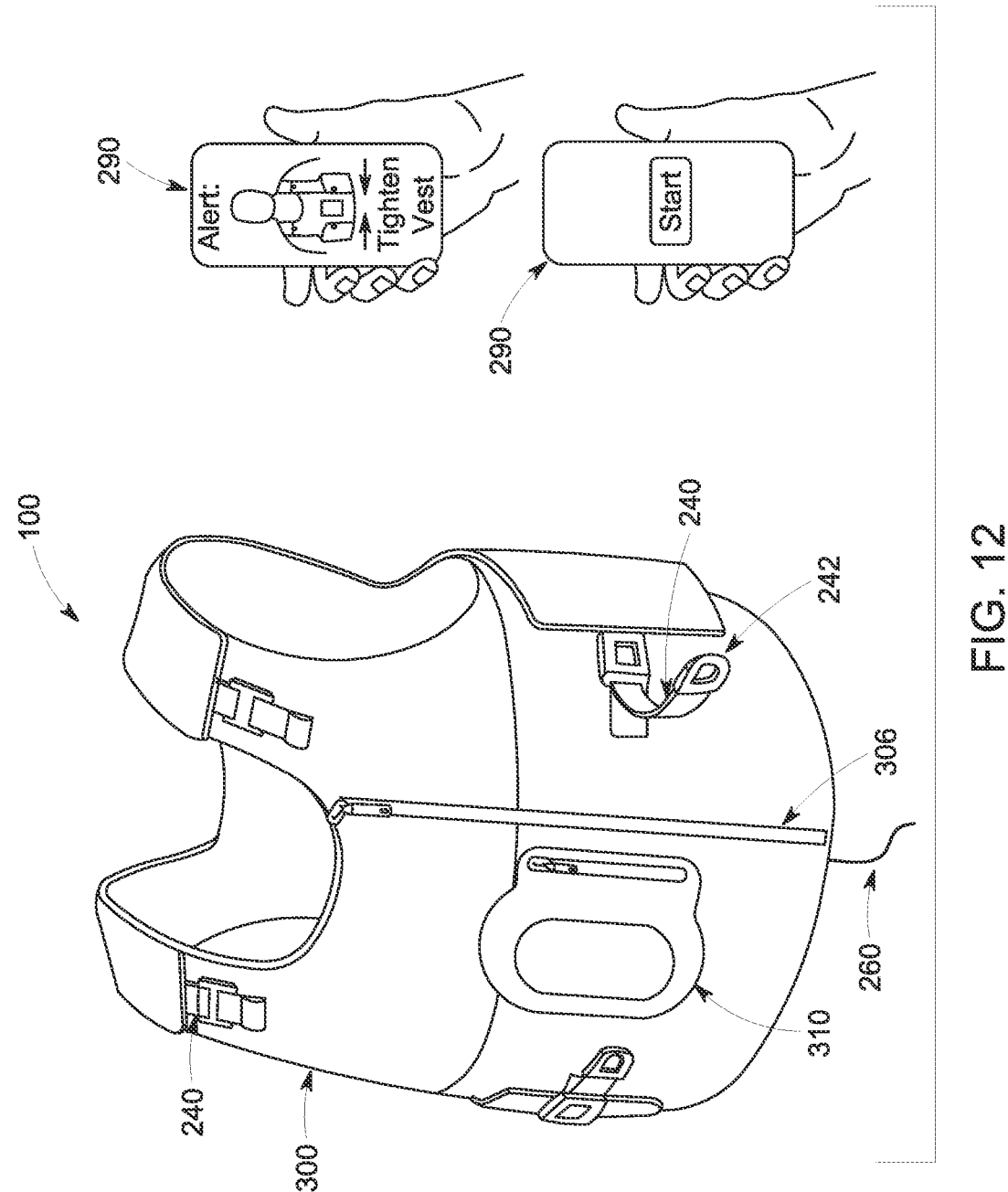
FIG. 12 depicts a wearable structure suitable for use as an ultrasound probe positioning structure, in accordance with aspects of the present disclosure.
Figure 13:
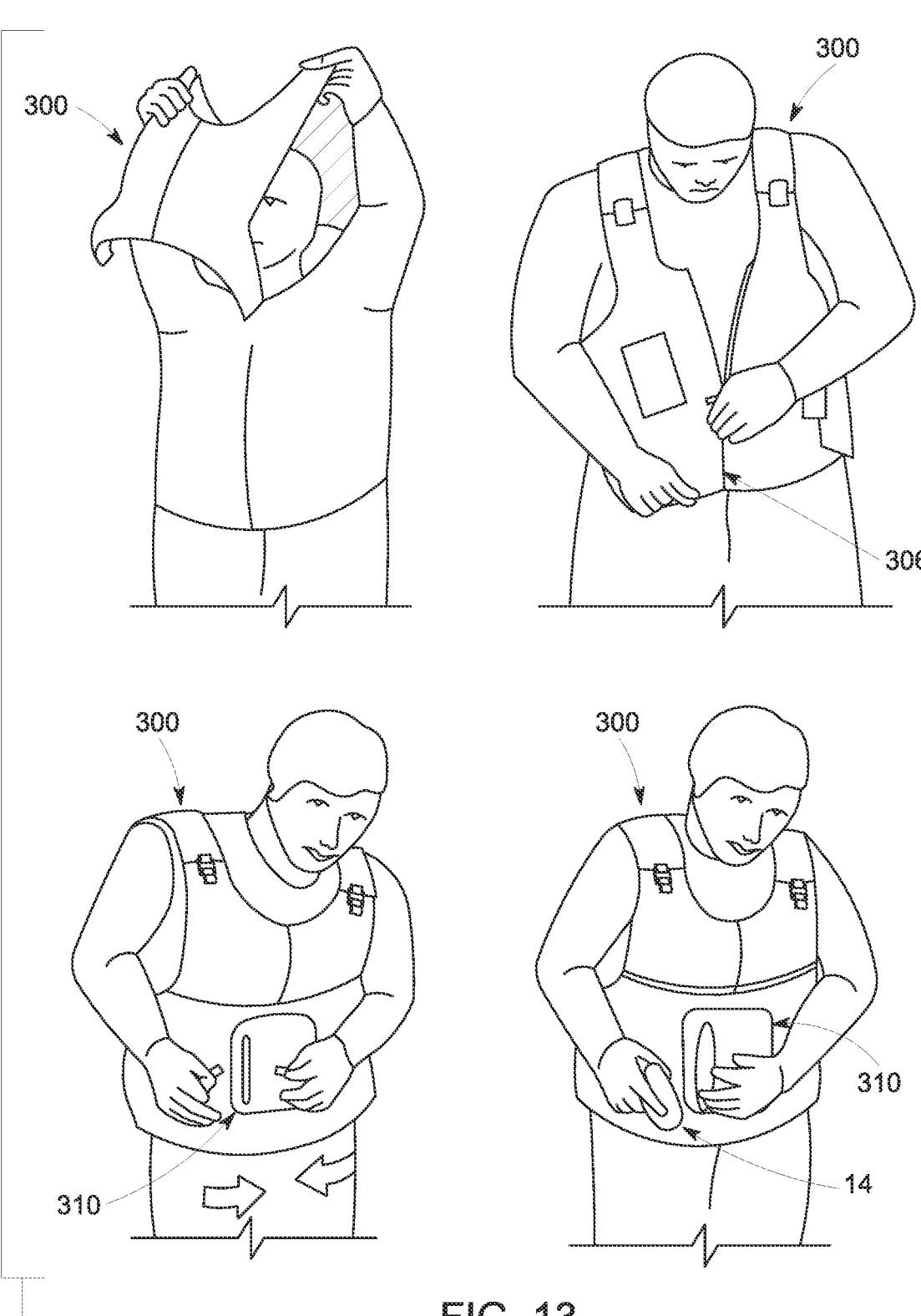
FIG. 13 depicts a sequence of cartoons illustrating application of the wearable structure of FIG. 12 to a patient, in accordance with aspects of the present disclosure.
Figure 14:
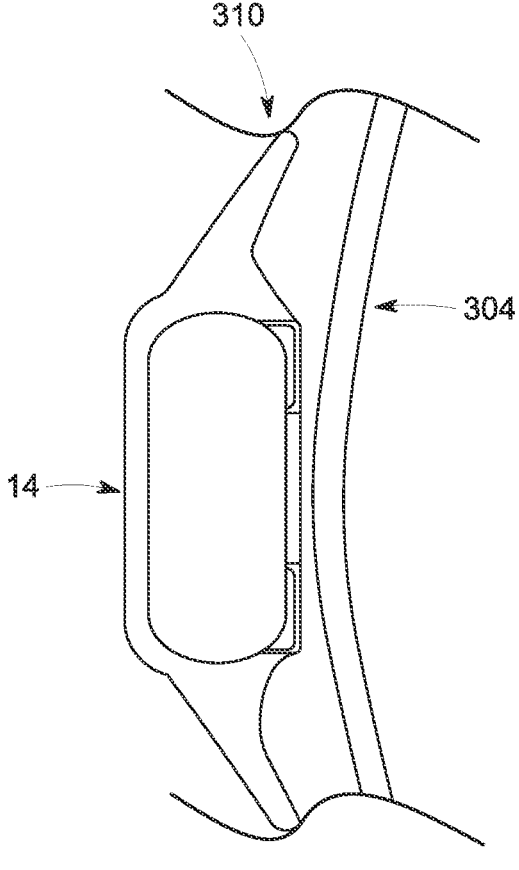
FIG. 14 depicts a probe holder pocket suitable for holding a probe module with respect to an ultrasound probe positioning structure, in accordance with aspects of the present disclosure.

Turning to FIGS. 12, 13, and 14, an example of a wearable structure 100 in the form of a vest 300 is illustrated that provides greater patient coverage and/or greater control of probe position. The vest 300 may be provided in multiple sizes (e.g., XS, S, M, L, XL) that fit different body sizes or types. As may be appreciated, in practice the vest 300 may be oriented or positioned to hold the probe module 14 in a clinically relevant position and orientation and thus the probe module 14 may be held on the front, back or side of the patient.

In the depicted example, the wearable structure 100 in the form of a vest 300 includes one or more tensioning features to facilitate fitting of a given vest 300 to a respective patient. For example, the implementation shown in FIG. 12 may be initially configured or fit in a fitting session and later applied by a clinician or by a non-clinician for therapy sessions.

By way of example, the vest 300 may be secured and released via a magnetic closure that is easy and quick to operate. In the alternative or in addition, one or more zippers 306 may be provided for securing the vest 300 when applied. Adjustments, in one implementation, may be accomplished using a pull-string tightening system, which is illustrated in FIG. 12 as including a pull string or strap 240 having a pull handle 242 and which controls the separation provided by one or more lace or webbing portions of the vest 300. By way of example, tightening of the pull string or strap 240 via the pull handle 242 may tighten a pull webbing portion of the vest 300 about the abdomen and/or shoulders of a patient and may be utilized to tighten (or loosen) portions of the vest 300.

In the depicted example, (and as shown in FIG. 14), the probe module 14 fits within a pocket 310 or other holder to be in contact with the patient's skin 304. The pocket 310 may be provided or formed integrally with the vest 300. By way of example, the pocket 310 may include a bracket or other structural feature with which the probe module 14 engages when inserted into the pocket 310. The pocket 310 may be constructed so as to ensure tension between the probe module 14 (when inserted) and the patient (i.e., when the probe module 14 is inserted into the fitted vest, the probe module 14 pushed into the body of the patient). When in the pocket 310, a cord 260 associated with the probe module may be routed through the vest 300 (e.g., through layers or passages formed within the vest 300.

Turning to FIG. 13, a sequential series of illustrations are provided illustrating an example, of a patient donning a vest 300 and inserting a probe module 14 into an integral pocket 310. As shown in this example, the patient initially dons the vest 300 over his head (upper left). The sides of the vest 300 are then secured, such as via magnetic closures and a zipper 306 is used to secure the vest 300 in a vertical direction (i.e., top to bottom) (upper right). Pull strings 240 may be pulled to tighten the vest 300 about the abdomen and/or shoulders of the patient (lower left). A probe module 14 may then be secured with a pocket 310 of the vest (lower right).

In certain embodiments, and turning back to FIG. 12, the probe module 14 may be configured to communicate with a processor-based device (e.g., a cellular telephone 290) which may implement or otherwise control operation of the probe module 14 and/or therapy module 12. For example, the cellular telephone 290 may store and execute an application that may facilitate electronic troubleshooting or alignment. By way of example, once the fitted vest 300 and probe module 14 are applied to the patient, the patient may utilize an application on a cellular telephone to perform an automatic adjust or alignment process that may electronically align and steer the therapy beam so as to address small misalignments.

Certain of the preceding implementations reference a fitting operation or session for adjusting a probe positioning structure as discussed herein. Such a fitting session may be employed for a first-time setup of a probe positioning structure for a respective patient and therapy protocol. In such a fitting session, patient-specific physical adjustments to the wearable structure 100, imaging parameters, and access location are all determined and recorded, such that the wearable structure 100 may be reconfigured at any time for that patient. In contrast to the fitting session, a dosing session is the normal mode of operation (i.e., application of a treatment), where the patient or another non-clinician operates the fitted wearable structure 100, such as on their own in their home. In an example of one such dosing session, the patient puts on the fitted wearable structure 100 (e.g., personalized body-worn device) while receiving system guidance and until alignment of the ultrasound image to the target is found. The system then operates in a hands-free autonomous manner until the treatment dose is complete.

Figure 15:
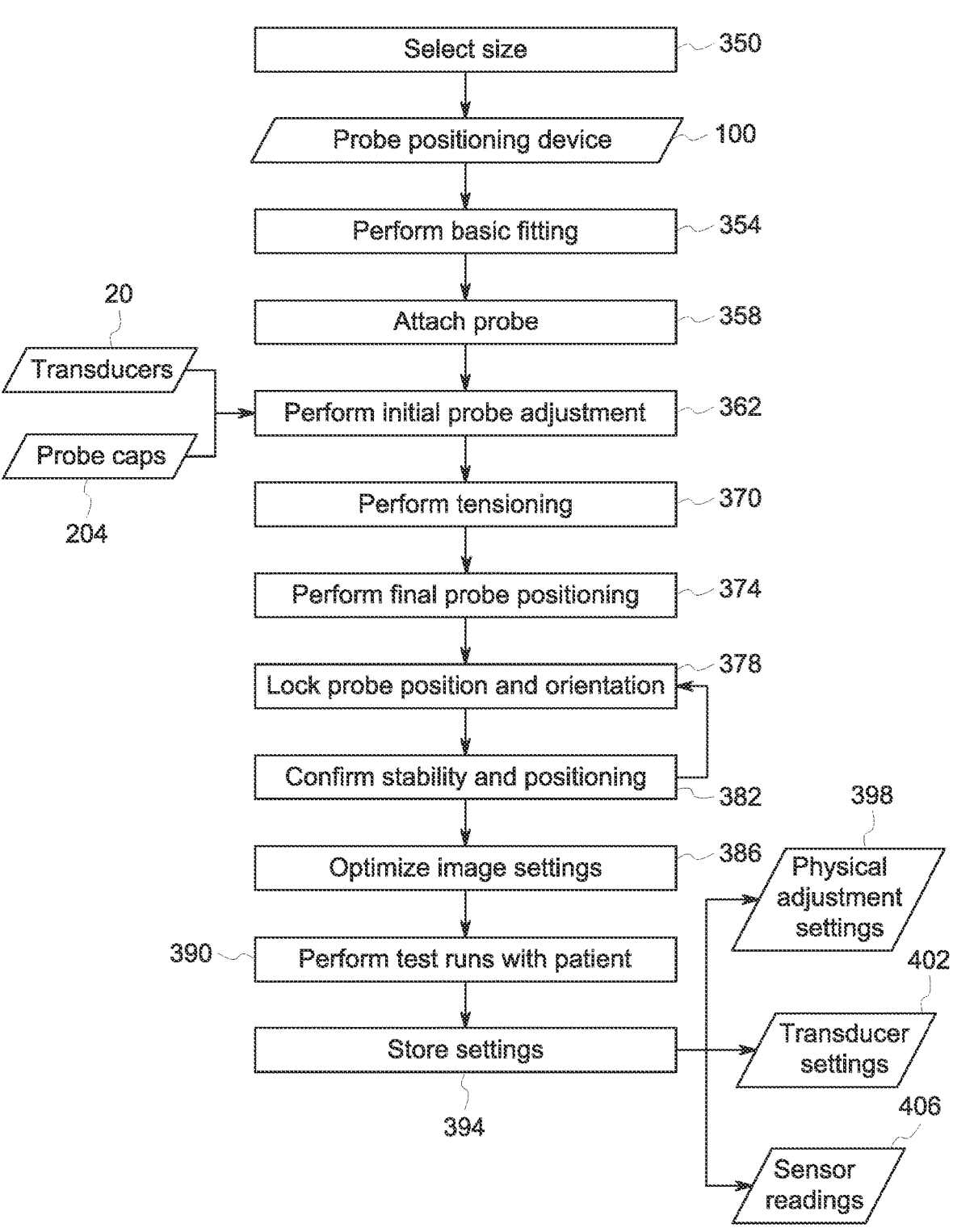
FIG. 15 depicts a process flow illustrating steps in fitting an ultrasound probe positioning structure, in accordance with aspects of the present disclosure.

Turning to FIG. 15, an example of steps performed in a fitting session is illustrated in the form of a process flow. It should be appreciated that the described steps and their sequence is merely provided for illustration and, in practice, certain actions may be performed in a different sequence or in parallel to one another. Indeed, the described steps and their order are merely provided for the purpose of illustration and to provide one example of a real-world context and implementation, and should not be viewed as limiting.

Turning to FIG. 15, in implementations where a wearable structure 100 comes in more than one stock size or type, a clinician may initially select (step 350) the size (e.g., small, medium, large) or type (belt, vest) of the wearable structure 100 to be fitted to the patient. A basic fitting step may then be performed (step 354) for the patient using the selected wearable structure 100. By way of example, the clinician may secure the wearable structure 100 to the patient (e.g., strap the body-worn device onto the patient) and may adjust one or more features of the device to obtain a basic fit. The probe module 14 may then be applied (step 358) and an initial probe adjustment performed (step 362). By way of example, the initial probe adjustment may include, but is not limited to, the clinician maneuvering the probe module 14 in six degrees of freedom (x-, y-, and z-position, rock, tilt, and spin (e.g., roll, pitch, and yaw)) while the patient breathes normally in order to locate the target region and to position the access point or window (i.e., the x-, y-position) on the body of the patient. As part of this process, the clinician may select or swap components of the probe module 14 (such as the selected transducers 20 and/or probe cap 204) or the probe module 14 itself in order to obtain the best alignment, depth, power delivery, angular extent, and so forth with the target region within the constraints of the overall system. By way of example, at this stage a clinician may select an appropriate probe SKU (stock-keeping unit for a unique configuration) or part to best fit the determined configuration. Examples of this approach may include selecting a swappable therapy transducer that adjusts the nominal depth, frequency, power delivery, and/or axial focus location and/or a swappable probe cap that angles the probe module 14 to reduce the required rock or tilt angles on the body surface, attenuates or shapes the therapy beam, or fits the size of the acoustic aperture to best fit the access zone and anatomical target for the patient.

Once these initial steps are done, a tensioning step may be performed (step 370). During this step the clinician may tension the wearable structure 100 (e.g., belt or vest) to lock the access point (x-, y-position) into position. A final probe positioning step may be performed (step 374) after tensioning. During this step the clinician may perform fine adjustments in four degrees of freedom (z-position, rock, tilt, and spin) to find the optimal probe position for a therapy session. Such optimal probe position will typically be based on the target alignment being acceptable for a sufficient percentage (e.g., 60% 70%, 80%, and so forth) of the respiratory cycle. Such target alignment optimization may be based on, but is not limited to, the target being maintained in the center of the field of view, the target being within the imaging plane, the target being within the electronic steering capability of the probe module 14, and so forth.

Once final probe positioning is performed, the clinician may lock the probe module 14 in position (step 378). The clinician may then release the probe module 14 and confirm the stability (step 382) of the fit of the probe module 14 on the body. These steps may be iterated and repeated until the observed stability is determined to be satisfactory.

The clinician may optimize the imager settings (step 386) once the probe positioning has been finalized. By way of example, the clinician may optimize the imager settings to obtain the best image quality in implementations in which imaging is performed in support of, or as part of, therapy administration. The image settings, as described below may be stored for use going forward with the patient. Examples of the ultrasound image settings include, but are not limited to depth, gain, frequency, and other common parameters to maximize image quality.

Once the position and imager settings are established as set forth above, one or more test runs may be performed (step 390) with the patient. By way of example, the patient may be taught how to put on the wearable structure 100 and may be observed performing some number of trials (e.g., 1, 2, 3, 4, 5, and so forth) to test the repeatability of the fit. As part of the patient trial process, the clinician may repeat one or more of the earlier steps to provide a secure and repeatable fit of the wearable structure 100. Once the wearable structure 100 and probe module 14 are fitted and configured, system settings for the embedded imager and computing electronics are determined and stored for use going forward. By way of example, settings may be recorded and stored (step 394) for the physical adjustments 398 of the wearable structure 100. In addition, the clinician or system may record and store imager setting 402 and/or sensor readings 406 related to the fit of the structure 100 (e.g., contact force or tension, posture, and so forth). Such image and or sensor fit settings (e.g., sensor outputs) may be used in subsequent sessions to check and guide the fit of the wearable structure 100 in a non-clinical therapy context. Similarly, the location (depth and axial position) of the target within the optimal scan plane may be determined and stored for subsequent uses. The stored settings may be employed to guide a user at home (or in another non-clinical setting) to check proper fit of the wearable structure 100 when used in the non-clinical setting.

While the preceding relates to example steps in fitting a probe positioning structure, it should be appreciated that additional steps may be taken as part of a fitting session. For example, as part of such a session, patient-specific baseline imaging data may be acquired for automated processing. Similarly, mock dosing sequences may be performed to test performance.

It may also be noted that probe module 14 and or probe holder 200 design and/or selection may be an aspect of the fitting or design process. In particular, probe modules 14, probe holders 200, and specific combinations of probes and holders may vary in their range of motion extents when fitted and attached to the wearable structure 100. In particular, when a probe module 14 is moved as part of a fitting process, motion of one type may be limited by or dependent on other aspects of the probe's orientation. For example, the maximum "rock" orientation of a probe may be dependent on the tilt angle and/or spin angle of the probe. This dependency is a function of the design of the probe module 14 and of the probe holder 200 (e.g., of a ball capture mechanism of the holder with respect to the wearable structure 100).

With this in mind, probe modules 14, probe holders 200, and specific combinations of probes and holders may be designed to have specific or known characteristics with respect their motion dependencies and interrelationships. In this manner, a suitable probe module 14 and probe holder 200 may be selected in the fitting process.

With respect to the design and/or characterization of probe modules 14 and probe holders 200 in terms of their motion characteristics, certain techniques may be employed and are hereby described for completeness. In one such characterization technique, different combinations of probe modules 14 and probe holders 200 are optically tracked for relative orientation (for each frame acquired) with respect to a wearable structure 100 while moved through a full range of motion for different permutations of orientation. In one example, the relative orientation is computed for the probe and wearable structure (e.g., belt) using inverse kinematics and known models of the components in question.

To determine the range of motion extents a convex hull (i.e., a convex three-dimensional (3D) structure) of a Delaunay triangulation can then be created based on orientation range-of-motion values displayed in 3 space, where x-values=rock, y-values=tilt, and z-values=spin, the three angles describing the spherical joint. In practice, the convex hull may be an envelope generated using a 3-space point cloud derived from observed tracking data transformed to relative angular joint data while moving the tracked probe module 14 (fitted within a tracked probe holder 200) relative to the wearable structure 100. This triangulation surface for a given probe module 14 and probe holder 200 represents the extents of the range of motion as a convex surface. In this manner, for a given value in one orientation (e.g., a given "tilt") the extent of motion available for the other angles (e.g., "rock" and "spin") for a given probe module 14 and probe holder 200 may be determined. A similar approach could be used to determine the range-of-motion and configuration dependent limitations for a given probe and probe holder with a non-spherical joint or joints (i.e., prismatic and/or revolute). Alternatively, the convex hull may be generated from simulated relative motion of CAD models during the design process.

In practice, the outer boundary of the convex hull is of primary interest as it represents the extent of motion. That is, in this context, the boundary of the convex hull represents the configuration-dependent extends of the rock, tilt, and spin angle parameters for a given probe and probe holder combination, thereby defining the configuration-dependent range of motion envelope for the three orientation angles.

To simplify interpretation of the 3D structure corresponding to the convex hull, two-dimensional "slices" may be generated through the 3D structure along an axis so as to better view the range of motion for the other two orientation angles at a given point on the axis (e.g., "slicing" the 3D structure with the z=0, x-y plane.) This corresponds, conceptually, to holding one angle fixed while moving the other two angles and finding, within a plane, the limits of those angles for the fixed first angle (e.g., how much can one vary the rock angle and tilt angle for a fixed spin angle).

Figure 16:
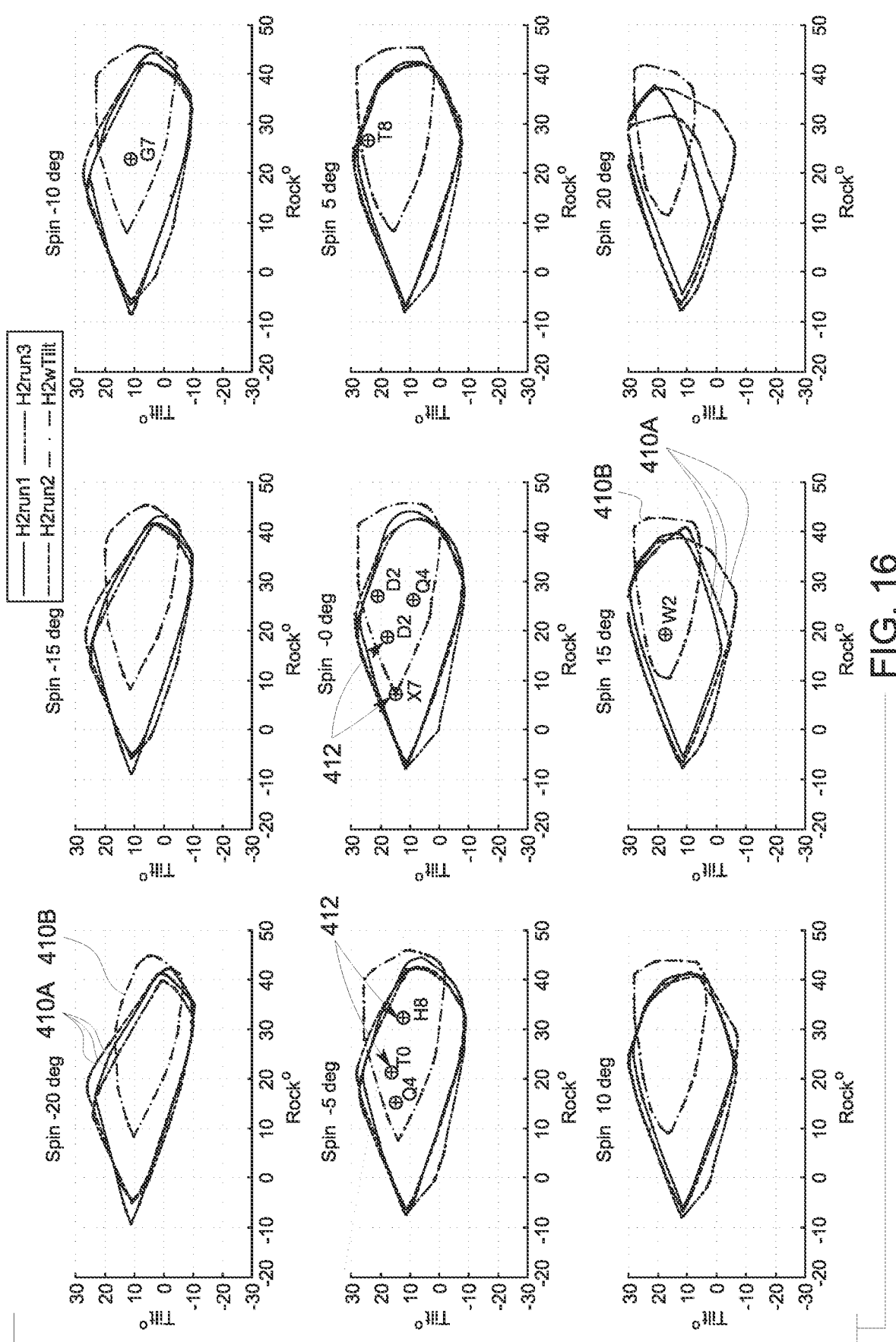
FIG. 16 depicts isoangle contours derived for multiple probe and wearable structure combinations, in accordance with aspects of the present disclosure.

This is illustrated in FIG. 16 as a series of isoangle contours 410, with each contour corresponding to a different position in the z-dimension (here the spin dimension) for a different probe/probe holder range of motion relative to a given patient (or wearable structure 100 in certain contexts). The edges of each isoangle contour 410 in this example show the range of motion for tilt (vertical axis) and rock (horizontal axis) for different probe/probe holder combinations at different values of constant spin (the different subplots). Using such techniques, different probe modules 14, probe holders 200, and/or combinations of probes and holders may be evaluated for suitability in a fitting operation as discussed herein. In the example illustrated in FIG. 16, two different combinations of probes and holders, 410a (H2run1, H2run2, and H2run3) and 410b (H2wTilt), are evaluated for suitability of fit for 7 different patients (collectively patients 412 (G7, T0, H8, Q4, X7, D2, W2)). Both probes and holders, 410a and 410b, can accommodate all 7 patients but probe and holder 410b may be undesirable since it leaves little margin for rock and tilt adjustment at the configured spin angle for patient X7. Herein, probe and holder 410a provides a more suitable fit for all of the 7 different patients. Similarly, a probe module 14 and/or probe holder 200 may be designed to provide a desired range of motion utilizing these techniques for evaluating range of motion or, alternatively, existing designs may be compared in terms of their range of motion.

The preceding discussion relates examples in which the wearable structure 100 or an aspect of the wearable structure 100 is a configurable garment or item that may be adjusted via various fitting structures or techniques (e.g., pull straps used to tighten webbing, adjustable or trimmable straps, inflatable air bladders, and so forth). In other embodiments, the wearable structure 100 (or component(s) to be used in conjunction with probe positioning structure, such as a customized transducer placement fixture or plate), may instead be manufactured or otherwise constructed based on the individual patient's body. That is, instead of being an adjustable "one size fits all" device or garment or having discrete size bins of customizable devices or garments, each individual wearable structure 100 or component(s) used in conjunction with probe positioning structure may be constructed based on the body of the patient so as to be unique to that patient. Thus, in such an implementation, the fitting process or session may instead be performed to parameterize and construct a custom-fitted wearable structure 100 or component specific to the patient, such as a custom-fitted probe interface device, as opposed to adjusting a more general wearable structure 100 or component to fit the patient.

Figure 17:
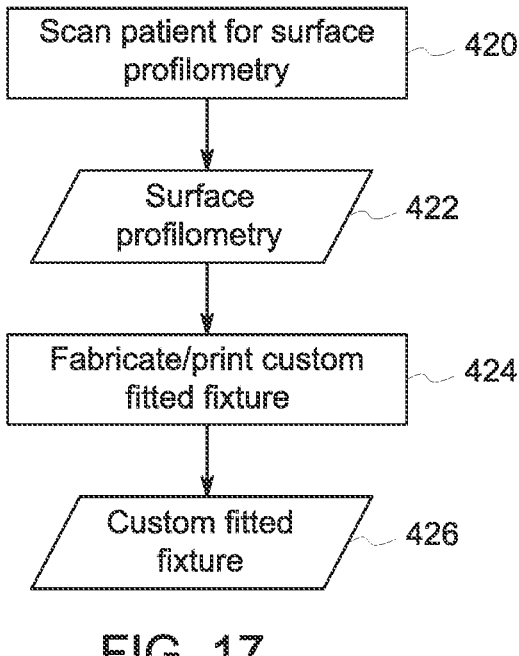
FIG. 17 depicts a process flow illustrating steps in fabricating a custom fitted fixture using surface profilometry and additive manufacturing, in accordance with aspects of the present disclosure.

By way of example, and turning to FIG. 17, in one implementation, a patient may be digitally scanned (step 420) for surface profilometry 422 using an infrared depth sensor, laser scanning technology, or other anthropometric means. The surface profile scan may be conducted in a clinical setting (e.g., in the clinician's office) or in a non-clinical setting (e.g., at the patient's home using a portable system and traveling operator or performed by the patient themselves, such as using a cellular telephone application that uses profile scanning technology). Such a scan may, in one embodiment, take less than one minute (e.g., 30 seconds) and may provide certain advantages, such as being able to be performed without patient contact and while the patient remains clothed (e.g., form-fitting clothing) thus allowing patient privacy.

The digital surface profile scan data (e.g., surface profilometry 422), however obtained, may be used to fabricate a custom-fitted fixture 426 (e.g., an ultrasound probe interface device) used to hold and position a probe module 14 relative to the patient during a treatment session. The custom-fitted fixture 426 may include, but is not limited to, a transducer mounting plate affixed to or integral with a custom fabricated component that conforms to the patient anatomy. With respect to fabrication of such a custom-fitted fixture 426 based on the surface profile scan data 422, such a fixture may be additively manufactured (e.g., 3D printed) or otherwise manufactured (step 424) using a suitable custom manufacture technique. For example, with respect to a transducer mounting plate being incorporated with a custom-fitted fixture 426, since only one custom plate is needed, a 3D printing approach may be suitable. In such an implementation, the patient-facing side of the fixture may have a geometry determined by the surface profilometry 422 while the opposite face or surface (i.e., the exposed side) may have a common transducer mounting flange to which the probe module 14 attaches. This approach may enable the transducer assembly to be mounted to a custom-fitted fixture 426 that conforms to the patient anatomy.

Figure 18:
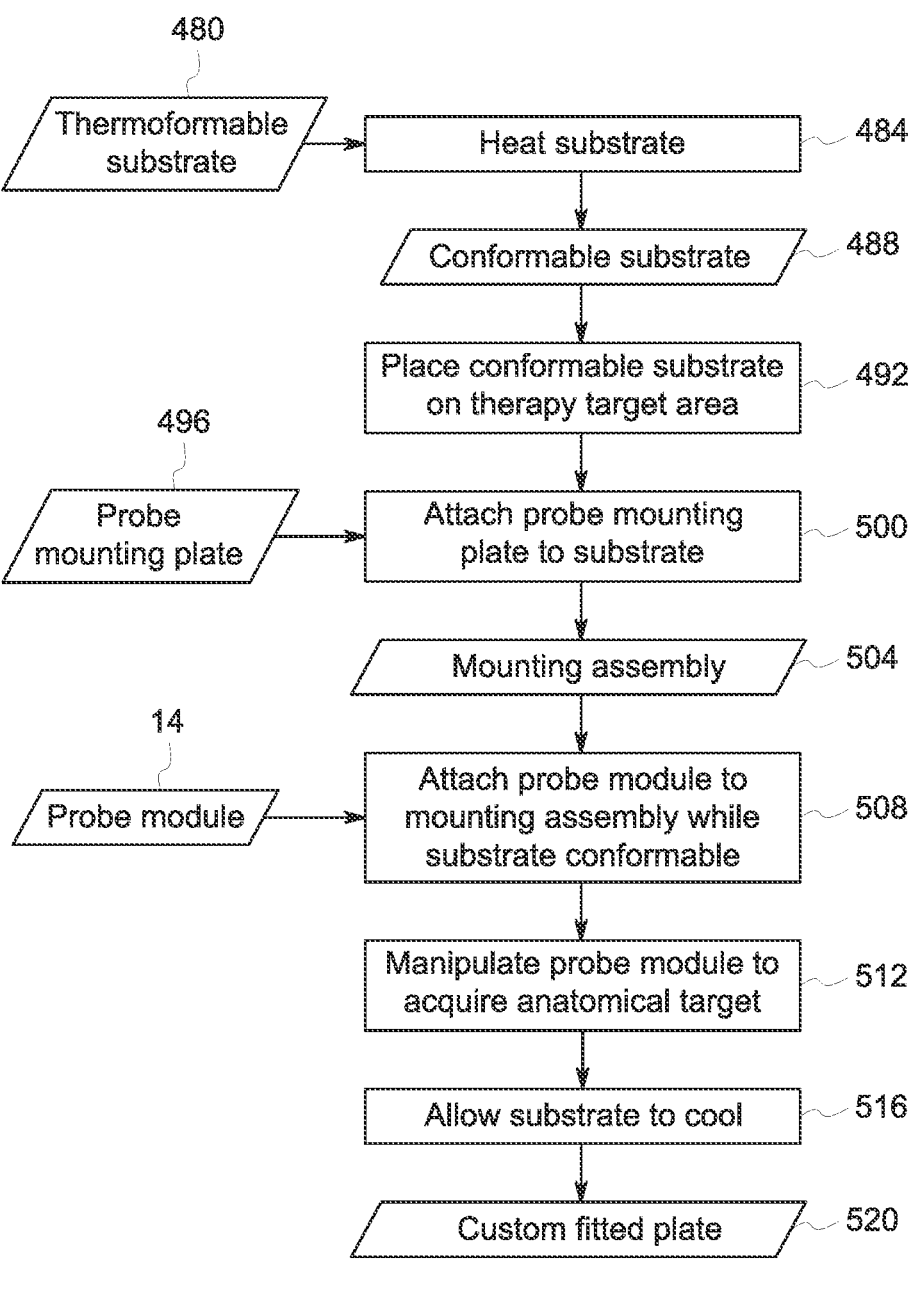
FIG. 18 depicts a process flow illustrating steps in fabricating a custom fitted fixture using thermoformable materials, in accordance with aspects of the present disclosure.

In another implementation, and turning to FIG. 18, a thermoformable (e.g., thermomoldable) custom-fitted plate may be formed, such as using a thermoformable substrate, in accordance with the process flow described. In one such example, a patient removes any intervening clothing and assumes the position to be adopted during a therapy session. A thermoformable sheet (e.g., thermos-moldable substrate 480), such as a thermoformable foam or polymer sheet, is heated (step 484) to form a conformable substrate 488, which is then placed over the therapy target area (step 492) and pressure applied to confirm the compliant thermoformable sheet to the underlying anatomy. In such an embodiment, the patient contact time may be five minutes or less). In one embodiment, the substrate (e.g., sheet) has an opening (e.g., central window) exposing the therapy target area, and is surrounded by a pressure sensitive adhesive. The therapy transducer mounting assembly (e.g., probe mounting plate 496) is bonded to this perimeter of adhesive (step 500) to form a mounting assembly 504. While the substrate is still conformable, a probe module 14 having a therapy transducer is introduced (step 508) to the mounting assembly 504 and manipulated (step 512) to acquire the anatomical target. The patient remains in the therapy body position while the substrate is allowed to cool (step 516) and become rigid, forming a solid mount for the transducer assembly in the form of a custom-fitted plate 520 that conforms to the body of the patient. A belt, garment, or other mechanism may then be used to secure the custom-fitted plate 520 to the patient for a therapy session.

Figure 19:
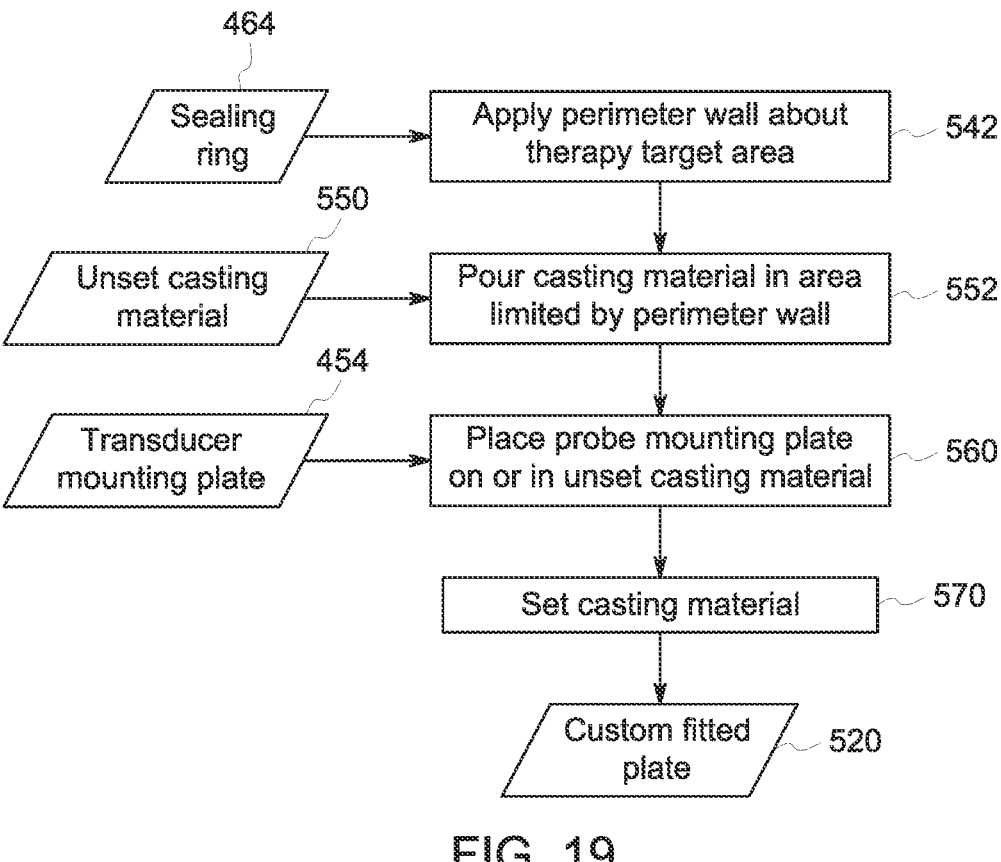
FIG. 19 depicts a process flow illustrating steps in fabricating a custom fitted fixture using casting techniques, in accordance with aspects of the present disclosure.
Figure 20:
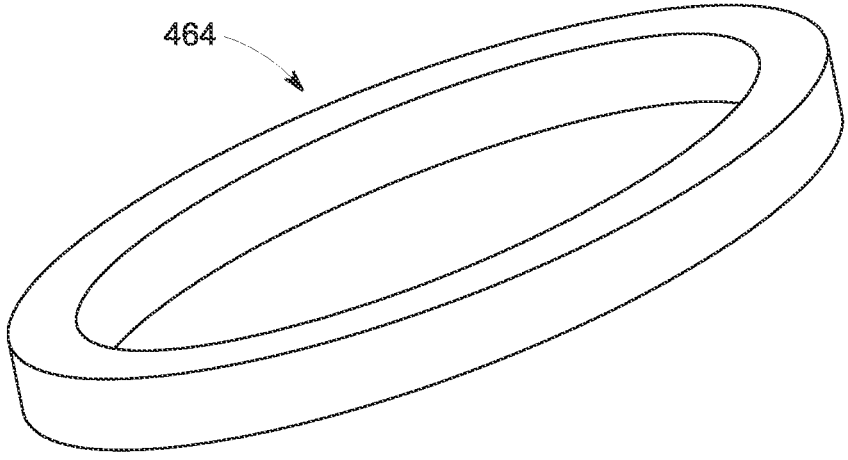
FIG. 20 depicts a sealing ring, in accordance with aspects of the present disclosure.

Turning to FIG. 19, in a further embodiment, a material having an unset (flowable or moldable) state and a set (solid) state may be used to form an impression of the body of the patient at the site where the transducers 20 will contact the patient. By way of example, in one implementation quick curing two-part silicone may be employed as a liquid casting material in conjunction with a perimeter wall (e.g., adhesive foam sealing ring 464) to limit the area of the casting. Alternatively, in another embodiment, the casting material may be plaster, expanding foam (e.g., fast curing foam in a bag), or a similar material that is moldable when not set. Turning to FIG. 19, this may be represented as generalized steps of a process flow as illustrated. In this example, the sealing ring 464 (i.e., perimeter wall) is applied (step 542) at the target therapy area while the patient is in the therapy position in order to define a region for forming a casting. The sealing ring 464 may be an adhesive backed foam structure that sticks temporarily to the therapy target area. An example of one such sealing ring 464 is shown in FIG. 20.

Figure 21:
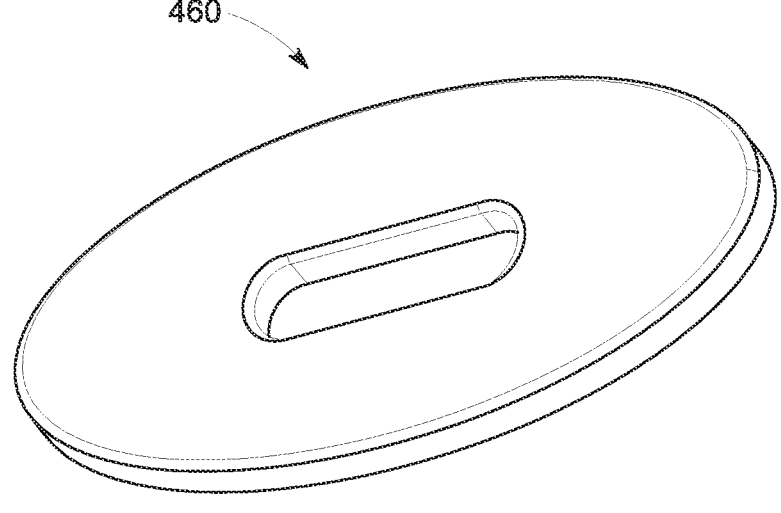
FIG. 21 depicts a molded body impression, in accordance with aspects of the present disclosure.

The unset casting material 550 (e.g., uncured silicone, unset plaster) may be poured (step 552) into the area defined by the sealing ring 464 and conform to the patient anatomy in this defined region so as to form a molded body impression 460 when set. The sealing ring 464 blocks the flow of the unset casting material 550 and allows for sufficient height (e.g., thickness) of the casting material to build up to form the desired molded body impression 460, an example of which is shown in FIG. 21. In some contexts pressure may be applied to the casting material to conform it to the patient, such as in an implementation where the casting material is an expanding foam in a bag and the bag is pressed against the patient anatomy. In certain implementations, the casting material is allowed to set for 7 to 10 minutes (e.g., for silicone or plaster) or 5 minutes or less (e.g., for expanding foam).

Figure 22A:
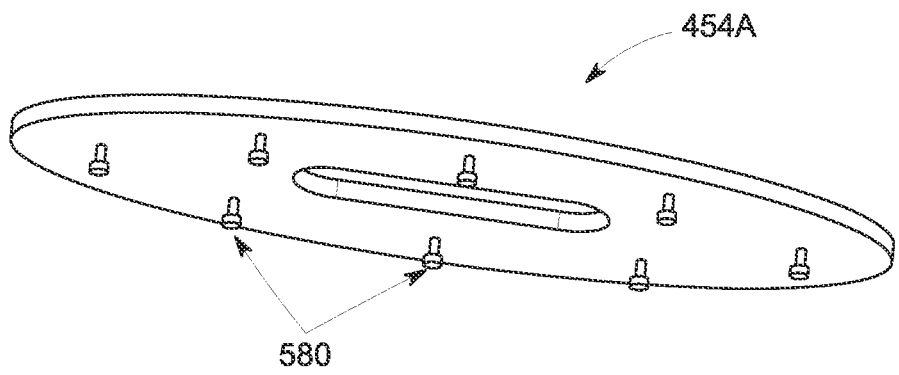
FIG. 22A depicts a transducer mounting plate, in accordance with aspects of the present disclosure.
Figure 22B:
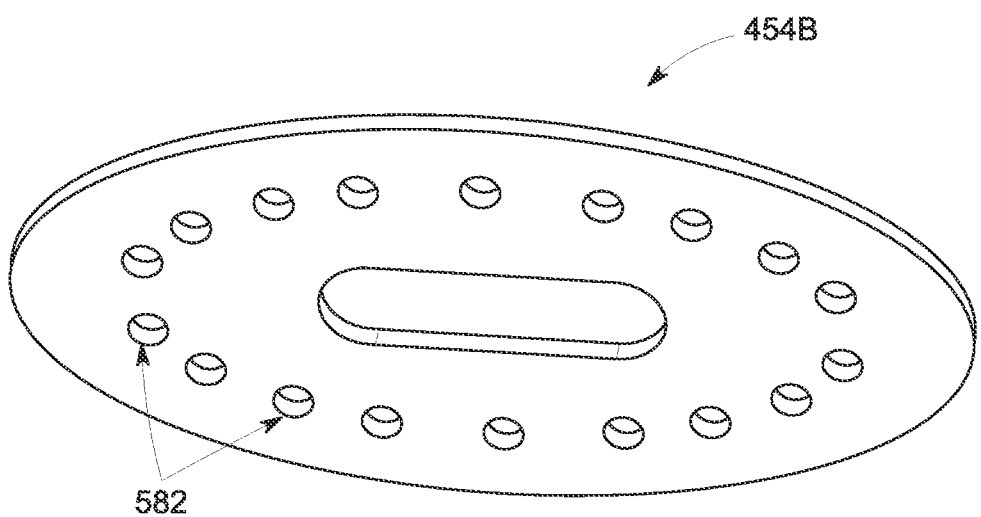
FIG. 22B depicts an additional transducer mounting plate, in accordance with aspects of the present disclosure.

A transducer mounting plate 454 (e.g., a rigid transducer integration plate) may be placed (step 560) on or into the unset casting material 550. In one embodiment, the transducer mounting plate 454 may have multiple anchors or bosses to mechanically lock the mounting plate 454 to the casting material after the casting material is cured (i.e., set). An example of such a transducer mounting plate 454A having anchors 580 is shown in FIG. 22A. Alternatively, as shown in FIG. 22B, the transducer mounting plate 454B could include multiple holes 582 throughout to allow casting material (e.g., silicone) to flow through and submerge the transducer mounting plate 454B, embedding the plate within the casting material when set.

Figure 23:
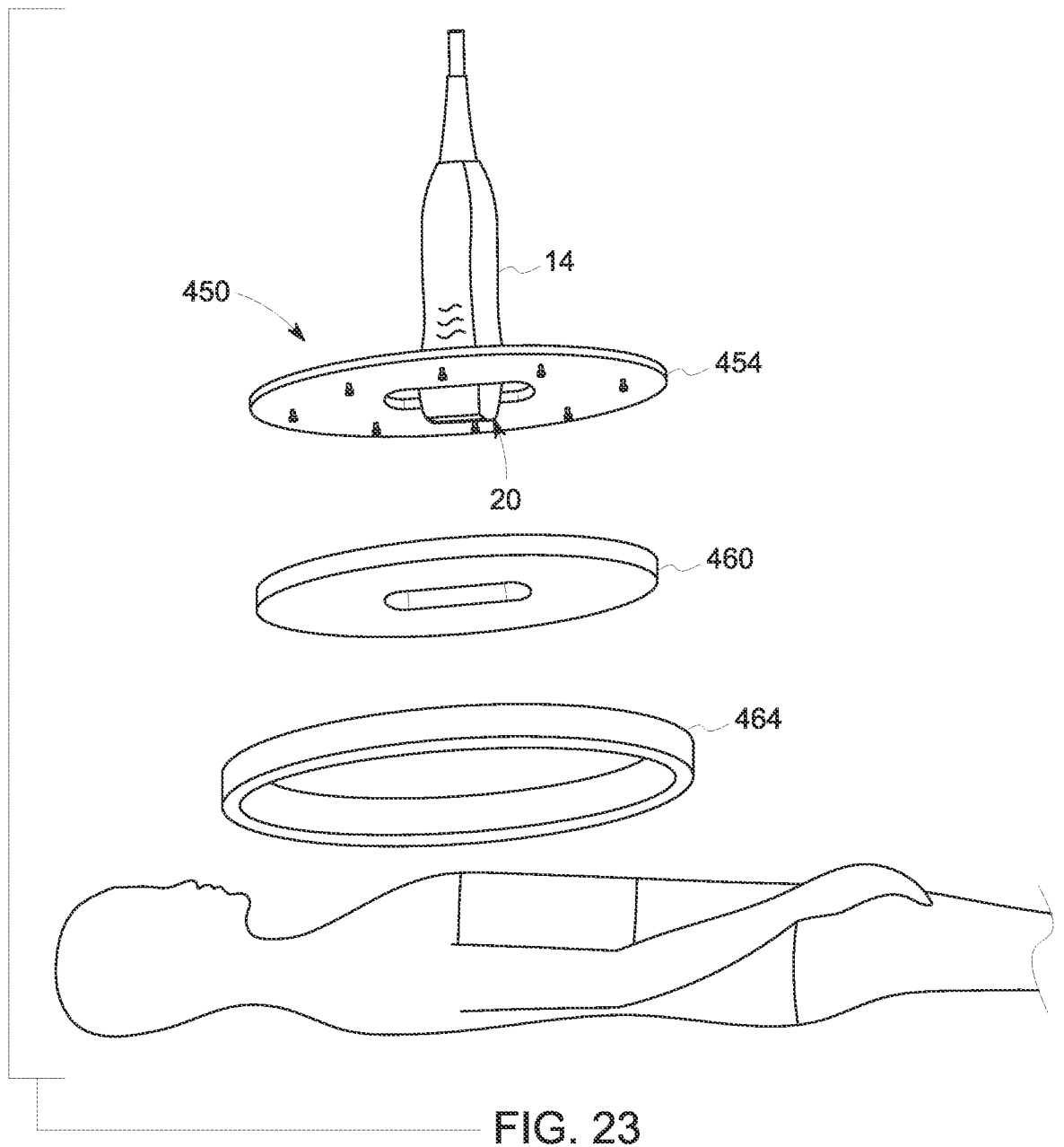
FIG. 23 depicts an exploded view of aspects of forming a custom fitted fixture, in accordance with aspects of the present disclosure.

As noted above, with the transducer mounting in position, the casting material may be set (step 570) using the appropriate environmental trigger(s) (such as temperature, time, chemical reaction, exposure to certain wavelengths of radiation (e.g., ultraviolet light) so as to solidify the casting material to the transducer mounting plate 454 and to provide a patient-conformable surface opposite the area provided for attachment of the probe module 14. In this manner, a custom-fitted plate 520 may be fabricated, which may be used with a belt or other attachment mechanism to secure to the patient, thereby allowing the probe module 14 to attach to the patient using a fixture custom-fitted to the patient. The relationship between the transducer mounting plate 454, probe module 14, molded body impression 460, and sealing ring 464 is shown in an exploded view in FIG. 23.

By way of example, for the respective examples described herein related to fabrication and use of a custom-fitted plate 520 for placement of a probe module 14 on a patient, various belts, vests, or other garments as described herein may be used to position and hold the custom-fitted plate 520 to the patient with the probe module 14 attached. By way of example, various belt assemblies may be used to hold and position the custom-fitted plate 520 (and attached probe module 14) for daily or periodic therapy. As discussed herein, the belt may be adjustable and could consist of a simple strap around the torso, multiple straps that could engage shoulders or other anatomical anchor points, or a full vest that contacts the full chest, sides, and back of the patient. As discussed herein, fit and adjustment of such a belt (or other positioning device) may be accomplished using systems or techniques as discussed herein. For example, tensioning of the device may be accomplished using elastic material, a ratcheting and locking cable tensioning system, pumped inflation, or lacing. Hook and loop fastening could be used to lock the belt into place after tensioning an elastic material. Further, the belt, vest, or other garment type device may incorporate rigid structures (e.g., straight or curved plates, rods, and so forth) which may help serve as mounting points for a probe module 14 or custom-fitted plate 520 and/or may help conform and "lock" to specific anatomical features (e.g., the ribs, spine, sides of the torso, and so forth). In such an implementation, such features may help prevent movement of the belt, vest, or other garment relative to the body once secured in place.

The preceding generally relates techniques for fabricating a customized, patient specific interface for probe module to contact a target area of patient anatomy (e.g., a custom-fitted plate 520. However it should also be appreciated that the custom-fitted structure may be more substantial or encompassing, such as a larger structure customized to fit to and confirm with a larger anatomic region, such as fitted to a torso, arm, leg, and so forth. Such custom-fitted structure may include, as described above, a region to which the probe module 14 is fitted or might otherwise be attached. In such approaches similar techniques as described herein may be employed to fabricate the customized structure, such as the use of formable or thermally pliable plastics or polymers (e.g., a thermoformable foam sheet or polymer), casting techniques using a settable material (e.g., silicone, plaster, expanding foam, and so forth) that sets subsequent to expansion, and so forth.

In addition to the above described approaches related to techniques for holding a probe module 14 to a target region of a patient in a repeatable and reliable manner, a further aspect of the present technique allows for full or partial target immobilization in order to facilitate non-clinical therapy applications. By way of example, target drift during neuromodulation therapy may occur due to respiration or patient movement. Such drift may make it difficult to maintain transducer alignment with the anatomic target.

To avoid such target drift, in some embodiments external pressure or constraints may be employed to reduce the extent of patient motion or eliminate patient motion with respect to the target treatment region and the point of contact of the probe module 14. In such contexts a probe module may be employed having less electronic steering capability, as such electronic steering may not be required to compensate for target drift.

By way of example, external pressure can be applied by pressing the transducer inward towards the target and a rigid clamp mechanism may be employed to exert the force required to locally displace the tissue between the transducer and target anatomy. The distance from transducer to target anatomy is also reduced as this tissue is displaced, allowing transducers of shorter focal depth to reach deeper target areas. A belt or other probe positioning structure as discussed herein may also be used to apply more general compression to the area, which would reduce target movement.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
an ultrasound probe, wherein, the ultrasound probe comprises one or more ultrasound transducers, wherein the one or more ultrasound transducers are configured to emit a therapy beam and the one or more ultrasound transducers are configured to emit an imaging beam;
a probe holder comprising a probe carriage frame, wherein the probe carriage frame comprises a passage that receives the ultrasound probe, and wherein the probe carriage frame is configured to move in a z-dimension, wherein the z-dimension comprises a linear axial dimension toward or away from a subject;
a wearable device comprising a belt or vest coupled to the probe holder and comprising one or more adjustable fitting features, wherein the one or more adjustable fitting features comprises tensioning features configured to hold the ultrasound probe against the subject with applied pressure; and
wherein the probe holder is configured to reversibly receive the ultrasound probe and to allow movement of the ultrasound probe to change a rock, a tilt, or a spin angular orientation of the ultrasound probe relative to an acoustic window of the wearable device.

2. The system of claim 1, wherein the one or more adjustable fitting features comprise one or more of straps, clips, ratchets, pull cords, lacing tensioners, or inflatable structures.

3. The system of claim 1, wherein the one or more ultrasound transducers comprise at least one ultrasound transducer that emits both the imaging beam and the therapy beam.

4. The system of claim 1, wherein the probe carriage frame is coupled to a rail to allow movement of the probe carriage frame and the ultrasound probe along the rail and towards or away from the acoustic window.

5. The system of claim 1, wherein the probe carriage frame is coupled to a spherical joint to allow movement of the probe carriage frame and the ultrasound probe to change one or more of the rock, the tilt, or the spin angular orientation.

6. The system of claim 5, comprising a joint clamp that is configured to reversibly secure the spherical joint in position.

7. The system of claim 1, wherein the probe carriage frame is configured to be reversibly locked in position and/or orientation to secure an ultrasound probe position and/or orientation.

8. The system of claim 1, wherein the wearable device is configured to conformally fit to the subject.

9. A method of configuring a wearable device, comprising:

applying the wearable device to a subject, wherein the wearable device comprises a belt or a vest, wherein an ultrasound probe is coupled to a positioning structure of the wearable device via a probe holder, and wherein the ultrasound probe comprises one or more ultrasound transducers, wherein the one or more ultrasound transducers are configured to emit a therapy beam and the one or more ultrasound transducers are configured to emit an imaging beam;

adjusting the probe holder relative to the subject to change a rock, a tilt, or a spin angular orientation of the ultrasound probe, wherein the probe holder comprises a probe carriage frame, wherein the probe carriage frame comprises a passage that receives the ultrasound probe, and wherein the probe carriage frame is configured to move in a z-dimension, wherein the z-dimension comprises a linear axial dimension toward or away from the subject;

determining one or more fitting parameters of the wearable device, the positioning structure, or the ultrasound probe when aligned to an anatomic target region of the subject, wherein the wearable device comprises one or more adjustable fitting features, wherein the one or more adjustable fitting features comprise tensioning features configured to hold the ultrasound probe against the subject with applied pressure; and saving the one or more fitting parameters for use when the wearable device is subsequently applied to the subject for a therapy session.

10. The method of claim 9, wherein saving the one or more fitting parameters comprises locking the ultrasound probe in place using a locking mechanism to fix a position of a frame of the probe holder relative to the wearable device.

11. The method of claim 10 wherein the locking mechanism is provided as part of the probe holder that allows movement of the ultrasound probe in x-, y-, and z-dimensions and orientation angles, wherein the locking mechanism locks the ultrasound probe into the position in the x-, y-, and z-dimensions as well as locking an orientation of the ultrasound probe.

12. The method of claim 9, wherein, while performing the step of adjusting, guidance is received based on one or both of image data or sensor data of the ultrasound probe.

13. The method of claim 9, wherein the adjusting comprises moving a frame of the probe holder relative to the wearable device to adjust the ultrasound probe.

14. The method of claim 13, wherein the moving is along a rail coupled to the frame.

15. The method of claim 13, wherein the adjusting comprises using a spherical joint.

16. The method of claim 9, wherein the probe holder comprises a frame configured to move relative to the positioning structure when a lock of the probe holder is in an unlocked position and wherein the frame is in a fixed position relative to the positioning structure when the lock of the probe holder is in a locked position.

17. The method of claim 16, wherein the lock comprises a clamp.

18. The method of claim 17, wherein the clamp locks a spherical joint.

* * * * *